(12) United States Patent
Ghodbane et al.

(10) Patent No.: US 11,116,640 B2
(45) Date of Patent: Sep. 14, 2021

(54) POLYMER FILAMENT REINFORCED SCAFFOLD FOR PARTIAL MENISCUS REGENERATION

(71) Applicant: Rutgers, The State University of New Jersey, New Brunswick, NJ (US)

(72) Inventors: Salim A. Ghodbane, Piscataway, NJ (US); Charles Gatt, Jr., Skillman, NJ (US); Michael G. Dunn, Manalapan, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/484,901

(22) PCT Filed: Feb. 13, 2018

(86) PCT No.: PCT/US2018/017988
§ 371 (c)(1),
(2) Date: Aug. 9, 2019

(87) PCT Pub. No.: WO2018/148722
PCT Pub. Date: Aug. 16, 2018

(65) Prior Publication Data
US 2019/0380838 A1 Dec. 19, 2019

Related U.S. Application Data

(60) Provisional application No. 62/458,368, filed on Feb. 13, 2017.

(51) Int. Cl.
*A61F 2/38* (2006.01)
*A61F 2/30* (2006.01)

(52) U.S. Cl.
CPC ........ *A61F 2/3872* (2013.01); *A61F 2/30942* (2013.01); *A61F 2/30965* (2013.01); *A61F 2002/30062* (2013.01); *A61F 2002/30576* (2013.01); *A61F 2002/30985* (2013.01)

(58) Field of Classification Search
CPC combination set(s) only.
See application file for complete search history.

(56) References Cited

U.S. PATENT DOCUMENTS

| | | | |
|---|---|---|---|
| 4,880,429 A | 11/1989 | Stone | |
| 5,007,934 A | 4/1991 | Stone | |
| 6,803,095 B1 | 10/2004 | Halladay et al. | |
| 7,993,391 B2 | 8/2011 | Stinson | |
| 9,226,992 B2 | 1/2016 | Mann et al. | |

(Continued)

FOREIGN PATENT DOCUMENTS

| | | |
|---|---|---|
| WO | 2006064025 A2 | 6/2006 |
| WO | 2011035017 A2 | 3/2011 |

(Continued)

*Primary Examiner* — Yashita Sharma
(74) *Attorney, Agent, or Firm* — Fox Rothschild LLP

(57) ABSTRACT

A resorbable scaffold for partial meniscus regeneration. The resorbable scaffold includes a polymer filament network and a matrix in the polymer filament network. The polymer filament network includes alternating layers of circumferentially-oriented filaments and radially-oriented filaments, and has a three-dimensional shape and geometry which is substantially the same as a three-dimensional shape and geometry of the resorbable scaffold.

18 Claims, 16 Drawing Sheets

(56) References Cited

U.S. PATENT DOCUMENTS

| | | |
|---|---|---|
| 2008/0112998 A1 | 5/2008 | Wang |
| 2009/0075382 A1 | 3/2009 | Sachlos |
| 2012/0265300 A1 | 10/2012 | Mauck et al. |
| 2014/0031933 A1 | 1/2014 | Gatt et al. |
| 2015/0150681 A1 | 6/2015 | Ricci et al. |
| 2016/0200043 A1 | 7/2016 | Thian et al. |

FOREIGN PATENT DOCUMENTS

| | | |
|---|---|---|
| WO | 2013116624 A1 | 8/2013 |
| WO | 20170214736 A1 | 12/2017 |

POLYMER FILAMENT REINFORCED SCAFFOLD FOR PARTIAL MENISCUS REGENERATION

RELATED APPLICATIONS AND CLAIM OF PRIORITY

This application is the U.S. National Phase of International Patent Application Serial No. PCT/US2018/17988, filed Feb. 13, 2018, which claims priority to U.S. Provisional Application No. 62/458,368, entitled Fiber-Reinforced Scaffold for Partial Meniscus Regeneration, filed on Feb. 13, 2017. The entire disclosures of the applications noted above are incorporated herein by reference.

FIELD

This document relates generally to medical devices. More particularly, this document relates to systems and methods for fabricating a soft tissue (i.e., fibrocartilage tissue) implant for partial meniscus regeneration.

BACKGROUND

The meniscus is a vulnerable area of the knee joint that is prone to acute and degenerative tears and injuries and comprised of 2 C-shaped menisci. The menisci are two C-shaped discs of fibrocartilage found between the condyles of the femur and the tibial plateau which play a critical role in the load transmission, load distribution, shock absorption, joint stability, and lubrication of the knee. Meniscus injuries affect nearly 1.5 million people per year in Europe and the United States, and are on the rise due to aging and increase in physical activity. The current gold standard for meniscal injuries is a partial meniscectomy, where the injured tissue is removed through arthroscopic surgery. Because the tissue has limited healing potential, the clinical outcomes of sub-total meniscectomies are generally poor. Moreover, there is correlation between the size of tissue removed and occurrence of osteoarthritis (follow up studies indicate that many patients developed osteoarthritis years after this surgical procedure, demonstrating a strong clinical need to develop better long-term solutions).

Another approach is that of tissue engineering. Current approaches include synthetic polymer scaffolds and collagen meniscus implants. With synthetic polymer scaffolds, polyurethane sponges are used to replace the meniscus. This approach has led to inconsistent results. Fibrocartilage growth is seen in some studies using this technology while in others fibrous tissue did not remodel into fibrocartilage. The underlying cartilage was protected in some studies but not protected in others.

Another type of meniscus implant uses a sponge containing collagen, hyaluronic acid and chondroitin sulfate. There is promising preliminary data for this implant, but it is not widely accepted by the orthopedic community because of issues with cytotoxic byproducts of cross-linking and scaffold shrinkage. Both of these approaches generate an amorphous structure, the mechanical properties of which may not be appropriate for a device designed to replace the meniscus.

Another alternative treatment is the use of biocompatible, resorbable scaffolds to replace damaged meniscal tissue. In this case, the following have been designed: a clinically useful meniscus replacement device with a fiber-reinforced meniscus resorbable scaffold having an intricate internal shape that can bear circumferential tensile loads. The strength of the scaffold is due to the many intersecting fiber reinforcements that distribute weight throughout the structure. This artificial weight-bearing tissue has a great potential in treating meniscus injuries. However, the current fabrication process is labor-intensive and requires weaving of a continuous fiber in distinct patterns. Such a continuous fiber weaving is not preserved if the scaffold need be cut into a desired shape or size. Hence, this process only allows fabricating pre-defined sizes of implants including limited matrix weaving patterns.

There remains a need for a tissue engineered scaffold with the necessary mechanical properties while allowing for diversity in treatment of meniscal damage of various shapes and sizes.

SUMMARY

In some embodiments, the present disclosure relates to a resorbable scaffold for partial meniscus regeneration. The resorbable scaffold may include a polymer filament network and a matrix embedded in the polymer filament network. The polymer filament network may include alternating layers of circumferentially-oriented filaments and radially-oriented filaments, and may have a three-dimensional shape and geometry which is substantially the same as a three-dimensional shape and geometry of the resorbable scaffold.

Optionally, the alternating layers of circumferentially-oriented filaments and radially-oriented filaments may be repeated in the polymer filament network such that cutting of the resorbable scaffold into a desired geometrical shape or size does not alter one or more mechanical properties of the resorbable scaffold.

In an embodiment, the resorbable scaffold may also include an attachment flap extending from an outer edge of the resorbable scaffold. The attachment flap may be configured to provide a substrate for cells to infiltrate after implantation of the resorbable scaffold from a host environment. Optionally, the attachment flap may be configured to extend outwardly from an upper outer edge or a lower outer edge of the resorbable scaffold.

In certain embodiments, the number of the circumferentially-oriented filaments is more than number of the radially-oriented filaments in the polymer filament network.

Optionally, the resorbable scaffold may be fabricated in the shape of a knee meniscus. Alternatively and/or additionally, the resorbable scaffold has a wedge-shaped cross-section. The wedge-shaped cross-section may be fabricated by reducing a length of the radially-orientated filaments of the polymer filament network along a vertical direction of the implant, and reducing a number of the circumferentially-oriented filaments of the polymer filament network along a vertical direction of the implant.

Optionally, filaments of the polymer filament network may be fabricated from a bioresorbable material. The bioresorbable material is selected such that a rate of degradation of the bioresorbable material is sufficiently long so as to allow for tissue ingrowth to occur within the bioresorbable material.

Optionally, the matrix may be fabricated from a bioresorbable material may be proteins, proteoglycans, biocompatible natural polymers, biocompatible synthetic polymers, and/or combinations thereof. The matrix may be fabricated from proteins including collagen. The collagen may be lyophilized and cross-linked. In certain embodiments, the filaments of the polymer filament network may be formed from poly(desaminotyrosyl-tyrosine dodecyl ester dodecanoate).

Optionally, the polymer filament network may be fabricated by three-dimensional (3D) printing.

In an embodiment, the resorbable scaffold may be configured so that a distance between each of the circumferentially-oriented filaments of the polymer filament network is inversely proportional to an aggregate compressive modulus of the resorbable scaffold.

In at least one embodiment, the resorbable scaffold may be configured so that one or more mechanical properties of the resorbable scaffold depend upon: the diameter of the circumferentially-oriented filaments, the length of the circumferentially-oriented fibers, the number of the circumferentially-oriented filaments, distance between each of the circumferentially-oriented filaments, the diameter of the radially-oriented fibers, the length of the radially-oriented fibers, the number of radially-oriented filaments, distance between each of the circumferentially-oriented filaments, and/or material of filaments of the polymer filament network.

Optionally, the resorbable scaffold is a knee meniscus implant that is configured to have at least one mechanical property that is substantially similar to that of an ovine native meniscus.

In an embodiment, a method for at least partial replacement of a damaged native meniscus is disclosed. The method may include replacing a damaged portion of the native meniscus with at least a portion of a resorbable scaffold according to claim 1 and corresponding to the damaged portion being at least partially replaced. The method may also include suturing the resorbable scaffold directly to the undamaged portion of the meniscus.

Optionally, replacing the damaged portion of the native meniscus with at least the portion of the resorbable scaffold may include cutting the resorbable scaffold to fabricate a partial scaffold having a three-dimensional shape and geometry which is substantially the same as a three-dimensional shape and geometry of the damaged portion being at least partially replaced.

In an embodiment, the method may also include suturing an attachment flap of the resorbable scaffold directly to the undamaged portion of the meniscus.

In one or more embodiments, the disclosure relates to methods and systems for fabricating a resorbable scaffold for partial meniscus regeneration. The method may include, by a processor, fabricating a polymer filament network by generating a digital model of the resorbable scaffold, determining a configuration of the polymer filament network from the digital model, translating the digital model into a series of computer-readable instructions for a 3D printer, and transmitting the computer-readable instructions to the 3D printer to print the polymer filament network. Translating the digital model into the series of computer-readable instructions may include slicing the digital model into a first set of slices corresponding to a plurality of circumferentially-oriented filaments and a second set of slices corresponding to a plurality of radially-oriented filaments. The method may also include printing, by the 3D printer, the polymer filament network in accordance with the computer-readable instructions. Printing the polymer filament network includes printing alternating layers of circumferentially-oriented filaments and radially-oriented filaments where the polymer filament network is configured to have a three-dimensional shape and geometry which is substantially the same as a three-dimensional shape and geometry of the resorbable scaffold.

In an embodiment, the method may also include infusing the polymer filament network with a matrix material by centrifugal casting. The centrifugal casting step may include positioning the polymer filament network in a negative mold to form a mold assembly, disposing a dispersion comprising the matrix material over the mold assembly, and centrifuging the mold assembly to infuse the polymer filament network with the matrix material. Optionally, the matrix material includes collagen containing proteins. The matrix material may also be lyophilized and cross-linked to fabricate the resorbable scaffold. Optionally, the cross-linking may performed using a 1-ethyl-3-(3-dimethyl aminopropyl) carbodiimide (EDC)/N-hydroxysuccinimide (NHS) solution. In an embodiment, the method may also include cutting the fabricated resorbable scaffold into a desired size and shape for use in partial meniscus regeneration.

Optionally, the resorbable scaffold is fabricated in a shape of a knee meniscus.

In one or more embodiments, generating the digital model may include generating the digital model using configuration data corresponding to the resorbable scaffold upon receiving the configuration data from a user and/or an image scanning device configured to provide image data of a native tissue.

Optionally, determining the configuration of the polymer filament network may include performing a geometrical analysis of the digital model relative to a large scale data base comprising magnetic resonance image (MRI) data corresponding to a native tissue that will be replaced by the fabricated resorbable scaffold.

In an embodiment, printing the polymer filament network may also include printing an attachment flap on an outer edge of the resorbable scaffold by halting the printing process before completion of the printing of the polymer filament network, prompting a user to place a support structure on an outer rim of a partially printed polymer filament network, resuming printing of the polymer filament network after said placement, such that print material is deposited on top of the support structure, and removing the support structure upon completion of the printing.

Optionally, thickness of each of the slices of the first set and the second set is equal to the diameter of a single filament of the polymer filament network.

Optionally, translating the digital model into a series of computer-readable instructions for the 3D printer may include selecting processing parameters. Alternatively, the step of selecting processing parameters may include selecting height of one or more slices, thickness of one or more slices, width of one or more slice, temperature, extrusion rate, printing head speed, and/or pre- and post-flow timing.

DESCRIPTION OF THE DRAWINGS

The present solution will be described with reference to the following drawing figures, in which like numerals represent like items throughout the figures.

FIG. 4A shows a single layer of circumferentially-oriented filaments. FIG. 4B shows a single layer of radially-oriented filaments. FIG. 4C shows a cross-section of the scaffold depicting the wedge shape characteristic of the scaffold and the optional attachment flap that may be used for fixation. FIG. 4D shows a 3D view of the complete scaffold.

DETAILED DESCRIPTION

Figure 1:
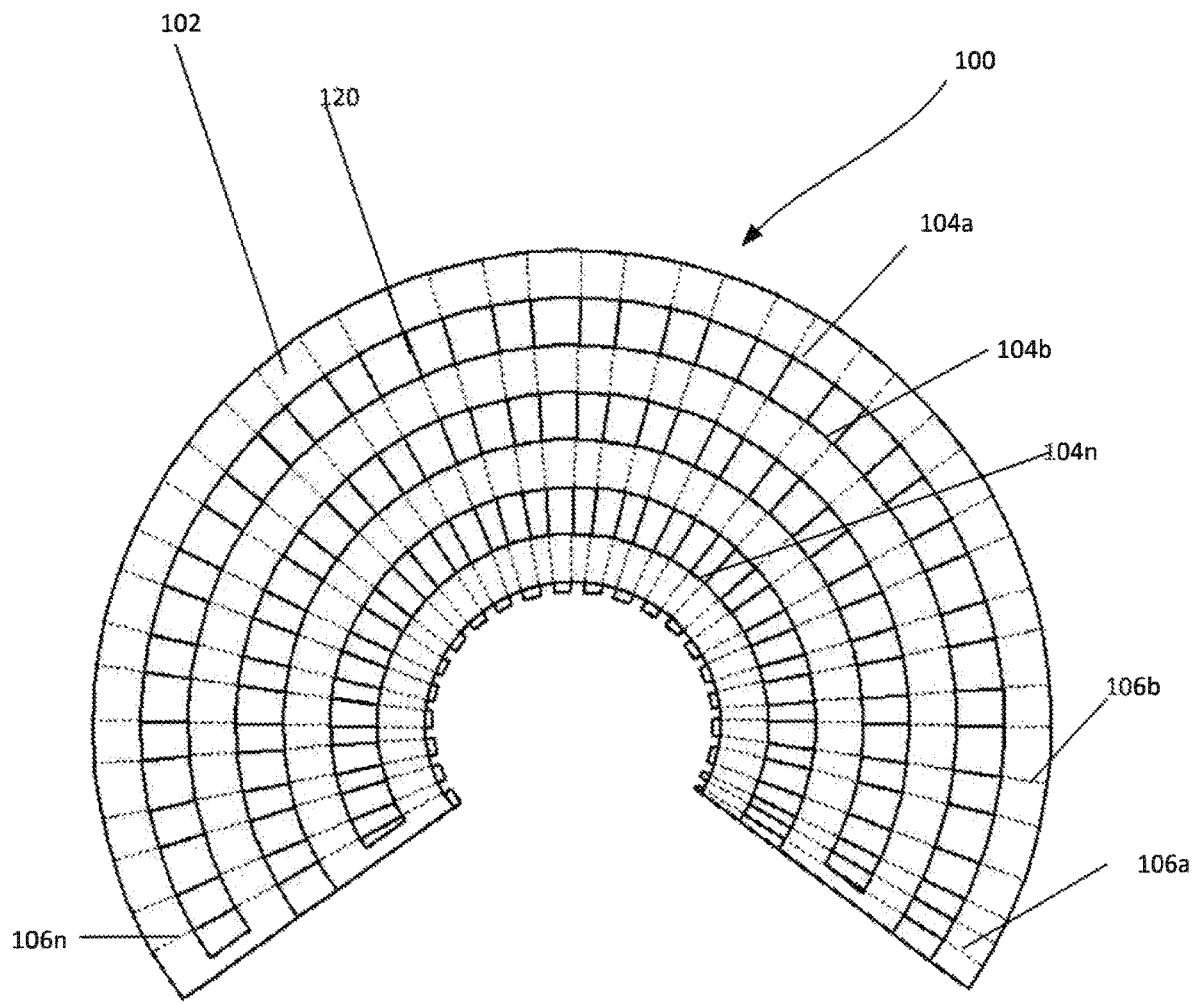
FIG. 1 is a top view of one embodiment of the resorbable scaffold illustrating a reinforcing polymer filament network.
Figure 2:
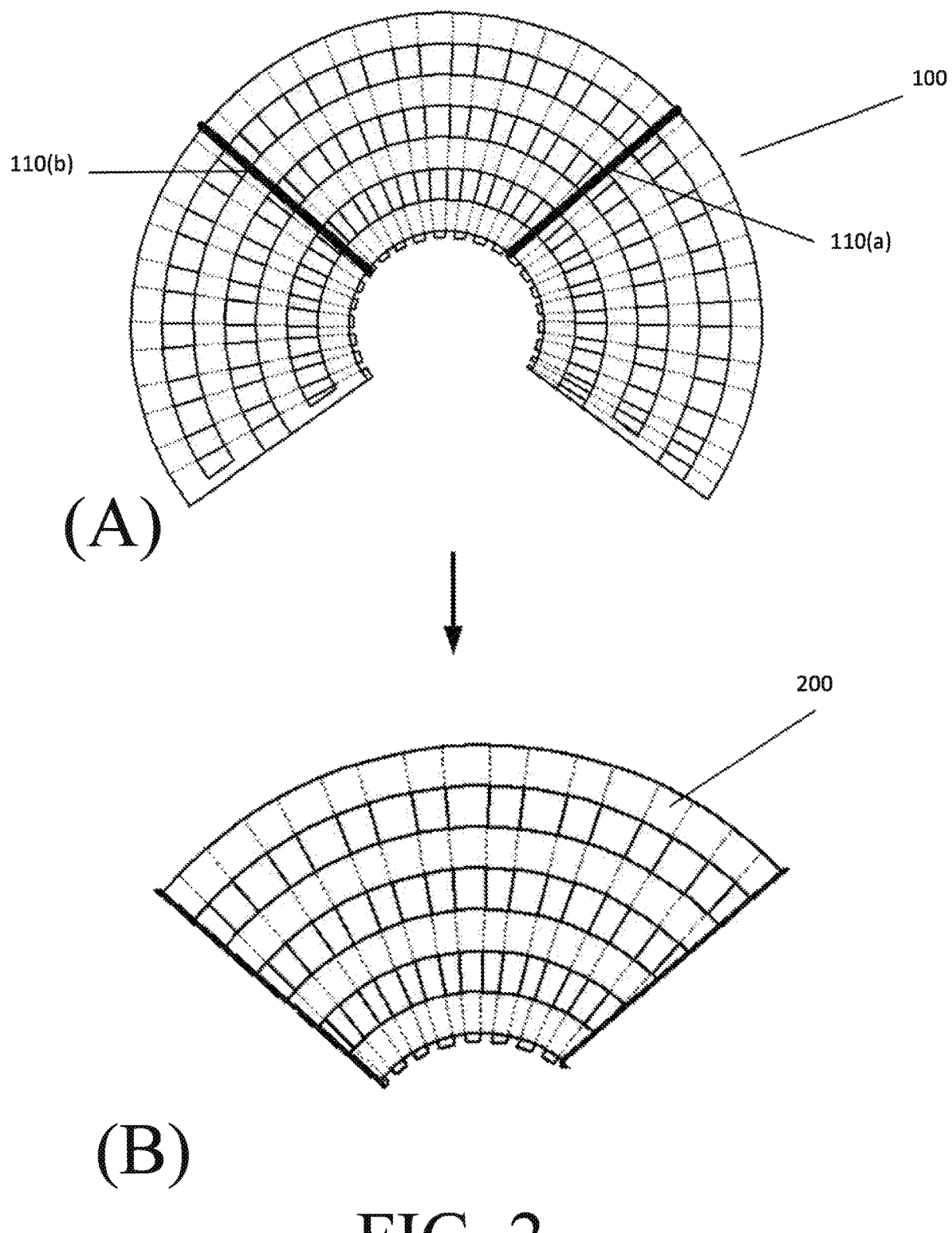
FIG. 2A is a top view of the scaffold of FIG. 1 illustrating example cut lines along which scaffold may be cut to form a scaffold for partial meniscectomy.
FIG. 2B illustrates a top view of the cut scaffold.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present solution may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

The term "about", as used here, refers to +/−10% of a value.

The terms "computing device" or "electronic device" refer to a device that includes a processor and non-transitory, computer-readable memory. The memory may contain programming instructions that, when executed by the processor, cause the computing device or electronic device to perform one or more operations according to the programming instructions. As used in this description, a "computing device" or an "electronic device" may be a single device, or any number of devices having one or more processors that communicate with each other and share data and/or instructions. Unless the context specifically dictates otherwise, the term "processor" will include embodiments having a single processor, as well as embodiments in which multiple processors collectively perform various steps of a process. Examples of computing devices and/or electronic devices include personal computers, servers, mainframes, printing devices having a processor and a memory, and portable electronic devices such as smartphones, personal digital assistants, cameras, tablet computers, laptop computers, media players and the like.

The term "implant" or "scaffold" refers to a composite structure fabricated in vitro comprising a matrix designed to replace a biological soft tissue in a subject and a polymer filament network designed to provide structural support to the matrix, that may be used to substitute at least part of a native tissue.

The terms "three dimensional printing", "3D printing" and rapid prototyping refer to collection of technologies for producing physical objects (e.g., tissue implants) directly from digital descriptions. Digital descriptions include output of any software that produces a 3D digital model, where the digital model guides a process by which multiple layers of a build material are formed and cured, typically under control of a computing device.

The terms "three dimensional printing device" and "3D print device" refer to a device or system that is capable of performing a 3D printing process. A 3D print device will include a processor. The processor will implement programming instructions, typically using parameters from a data file, that cause an applicator of the device to selectively deposit layers of a build material (such as a biodegradable polymer), and that cause a radiation generating device (such as a laser or heat source) to selectively apply energy to help cure the deposited layers of build material. As used throughout this disclosure, the terms "three-dimensional printing system," "three-dimensional printer," "3D print device," "3D printing system," and "3D printer" refer to any known 3D printing system or printer.

Engineered meniscal substitutes or implants serve as an attractive method to prevent or delay osteoarthritis following surgery by protecting underlying articular cartilage, providing mechanical support, and promoting tissue regeneration. Accordingly, the present document concerns the design and fabrication of an acellular, resorbable partial meniscus scaffold that can be implanted during a partial meniscectomy to improve patient prognosis following surgery. Meniscectomy is the surgical removal of all or part of a torn meniscus. In partial meniscectomy, only a part of the meniscus is removed (i.e., only the unstable meniscal fragments) and the remaining meniscus edges are smoothed so that there are no frayed ends. The current resorbable scaffold can be personalized by cutting it into an appropriate size based on the size of the part of the meniscus removed during partial meniscectomy and provides a template for a patient's own cells to remodel the tissue into new meniscus tissue during such partial meniscectomy. In the meantime, the resorbable scaffold also provides protection to the tibial and femoral articular cartilage in order to prevent, or at least delay, the onset of osteoarthritis.

There are many novel features of the present solution. For example, the present solution provides: a resorbable collagenous scaffold that includes a reinforcing polymer filament network that is 3D printed with a repeating pattern of alternating sets of polymer filaments in a circumferential direction and a radial direction. The polymer filaments may be printed using poly(desaminotyrosyl-tyrosine dodecyl ester dodecanoate) [p(DTD DD)]. Furthermore, the polymer filament network is infused with a matrix comprising hyaluronic acid-collagen dispersion via a unique centrifugal collagen casting technique. The polymer filament network may also be designed to provide a flap that will flank the remaining native meniscus rim. The flap provides a substrate for cells to infiltrate from the native synovium.

The basic concept of the present solution is a resorbable scaffold comprising a polymer filament network and infused with a matrix (e.g., a collagen-hyaluronic acid sponge). The 3D printed design provides anisotropic mechanical properties that better mimic the native meniscus mechanical properties (and which has been shown to promote fibrocartilage formation). The 3D printing also provides a highly interconnected polymer architecture that still maintains mechanical properties with cutting and shaping, allowing the surgeon to customize the resorbable scaffold at the point-of-use using partial meniscectomy. Specifically, the filaments of the polymer filament network are highly interconnected allowing a surgeon to shape the resorbable scaffold at the point-of-use for each unique meniscal defect geometry without unraveling the filament network.

The system and method of making a personalized partial meniscal resorbable scaffold will be described herein with respect to making of a knee meniscus implant. Although the instant resorbable scaffold is described in relation to making of a knee meniscus implant, the teachings of the instant disclosure may also be applied to making implants for replacing other tissues similar in nature and function to the meniscus, such as intervertebral discs, temporomandibular discs, wrist menisci, and the like. These tissues are similar to the knee meniscus in that they are composed of fibrocartilage and function as load transmitters and distributors to prevent high-stress cartilage-on-cartilage or bone-on-bone contact that is detrimental to the joint. It will also be understood that the instant teachings may be applied to make implants for both human and animal patients.

Exemplary implants will be described with reference to FIGS. 1-4. Referring to FIG. 1, there is shown a resorbable scaffold 100 comprising a matrix 102 and polymer filament network 120 embedded in or coupled to the matrix 102.

The matrix 102 generally comprises a material that has been engineered to cause desirable cellular interactions to contribute to the formation of new functional tissues for medical purposes and/or the replacement of portions of or whole biological tissues. For example, in an embodiment, the matrix 102 is engineered to have a porous structure to allow for host cells of the native tissue to infiltrate the scaffold and remodel the native tissue.

The polymer filament network 120 is an engineered structure generally configured to strengthen and/or support the matrix 102. As such, the polymer filament network 120 may also have the same general shape and geometry as the matrix 102, but with a greater density of material (e.g., filament) as compared to that of the matrix 102. The material can include, but is not limited to, natural materials, synthetic materials, biodegradable materials and permanent materials. The increased density causes the polymer filament network 120 to be stiffer than the matrix 102 such that the polymer filament network 120 provides structure support to the matrix 102. The structural support can include, but is not limited to, tensile support and/or compressive support.

In some scenarios, the porosity of the scaffold 100 is designed in accordance with a particular application. For example, the scaffold 100 is designed to have a relatively high porosity to ensure adequate tissue and cell infiltration there through. Any level of porosity can be used herein without limitation provided that is sufficient for facilitating adequate cell seeding, fluid flow and structural integrity.

In some scenarios, the scaffold 100 is used as a fibrocartilage implant (e.g., a knee meniscus, intervertebral disc and/or TMJ joint implant), a tendon implant, a ligament implant and/or cartilage implant.

The shape and geometry of the matrix, and consequently the scaffold, is based on the shape and geometry of the soft tissue in need of replacement. Thus, as shown in FIG. 1, in the case of a complete meniscus implantation, the matrix 102 may be constructed as a c-shaped disc with a wedge-like cross-section, similarly to a knee meniscus. Although not necessary, the polymer filament network may also have the same general shape and geometry as the scaffold. Furthermore, it may be shaped concave on the top, which would come in contact with femur, and flat on the bottom, which would rest on the tibial plateau.

For forming a partial meniscus scaffold, the c-shaped scaffold of FIG. 1 can be cut into a desired shape and/or size without affecting the structure of the scaffold (because of the properties of the polymer filament network). As shown in FIGS. 2A and 2B, the c-shaped scaffold can be cut along the lines 110(a) and 110(b), to for a scaffold for partial meniscectomy. Alternatively and/or additionally, in the case of a partial meniscus implantation, the matrix and the polymer filament network may be designed and constructed based on the shape and size of the native tissue that needs to be replaced to form a partial meniscus scaffold.

Referring back to FIG. 1, the polymer filament network 120 may be formed by a repeating pattern of alternating layers of polymer filaments in a circumferential direction and a radial direction. As used herein, the term "filament" refers to any generally elongated member consisting of a single component, e.g. monofilament suture, or multiple components, e.g. multifilament suture. The filaments of the polymer filament network are formed by 3D printing a polymer as discussed below. The physical property of the 3D printed filament, such as tensile strength, cross-sectional area, diameter, flexibility, etc., may vary over the length of the filament. In some embodiments, multiple filaments may be 3D printed to form the polymer filament network 120. The filaments may be made of the same or different materials and may follow the same or different paths. In some embodiments, the filaments 3D printed to form the polymer filament network 120 may be printed in two different arrangements: a circumferential arrangement 104 and a radial arrangement 106. The two arrangements may be printed in a repeating pattern of alternating layers and/or a different repeating pattern (discussed below)

Figure 3:
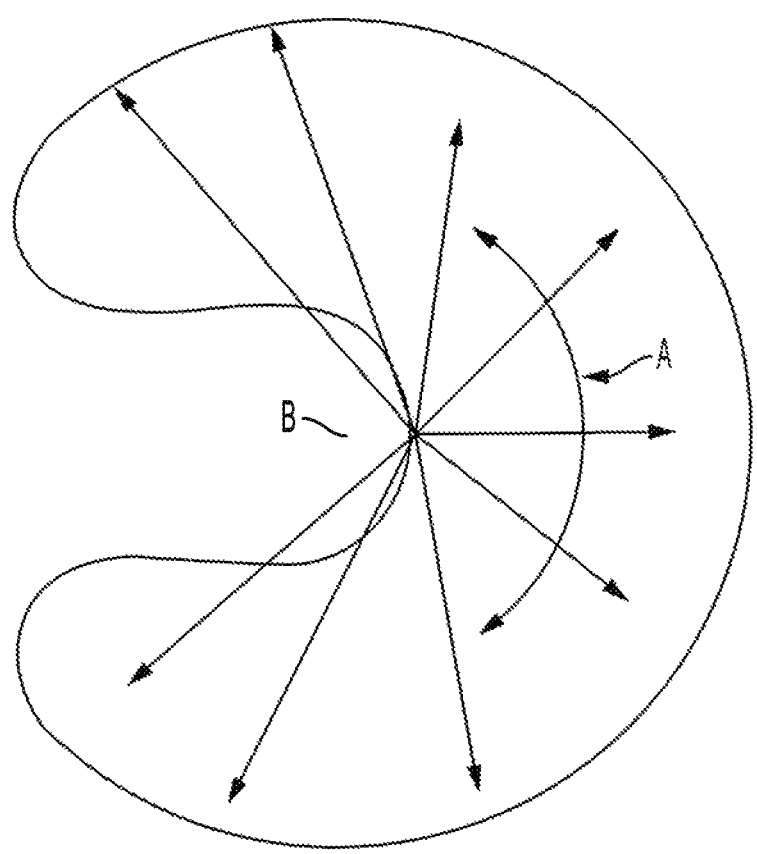
FIG. 3 is a top view of the device in FIG. 1 illustrating the directions of the circumferentially-oriented fibers and the radially-oriented fibers.

Referring to FIG. 3, for the purposes of the instant disclosure, the circumferential direction of the scaffold 100 is indicated by arrow A and the radial direction of the scaffold 100 is indicated by arrows B. The term "circumferential filament" refers to a filament that is positioned substantially parallel to the circumferential axis indicated by arrow A. The term "radial filaments" refers to filaments that cross the circumferential filaments at various angles to keep them from separating. Keeping the circumferential filaments from separating increases the durability and longevity of the scaffold, and also provides compressive mechanical strength to the implant. For convenience, terms "circumferential filament network" and "radial filament network" may be used herein to refer to multiple circumferential filaments or multiple radial filaments, respectively.

As used herein, the terms "radial arrangement," or "arranged radially," include, as one example, an arrangement of filaments extending in directions substantially parallel to arrows B in FIG. 3 at various angles in relation to the scaffold. Thus, the polymer filament network 120 comprises a first set of one or more circumferential filaments 104a, 104b, . . . 104n (collectively referred to as "104") and a second set of one or more radial filaments 106a, 106b, . . . 106n (collectively referred to as "106"), and the first set and the second set are arranged in a repeating pattern of alternating layers (or another arrangement). In vivo, as meniscal tissue grows into the scaffold 100 and cells attach to the filament networks, cells on or about the circumferential filaments 104 experience the same mechanical environment as in a normal meniscus, resulting in the formation of tissue with the essentially the same organization and directionality of collagen filaments as the original meniscus.

In an embodiment, the number of circumferential filaments is more than the number of radial filaments to provide the implant with higher tensile strength in the circumferential direction in order to, for example, better mimic the anisotropy of the native tissue. In other words, the filaments predominately run circumferentially with fewer radially oriented filaments to provide the tissue with high tensile properties in those directions.

Figure 4:
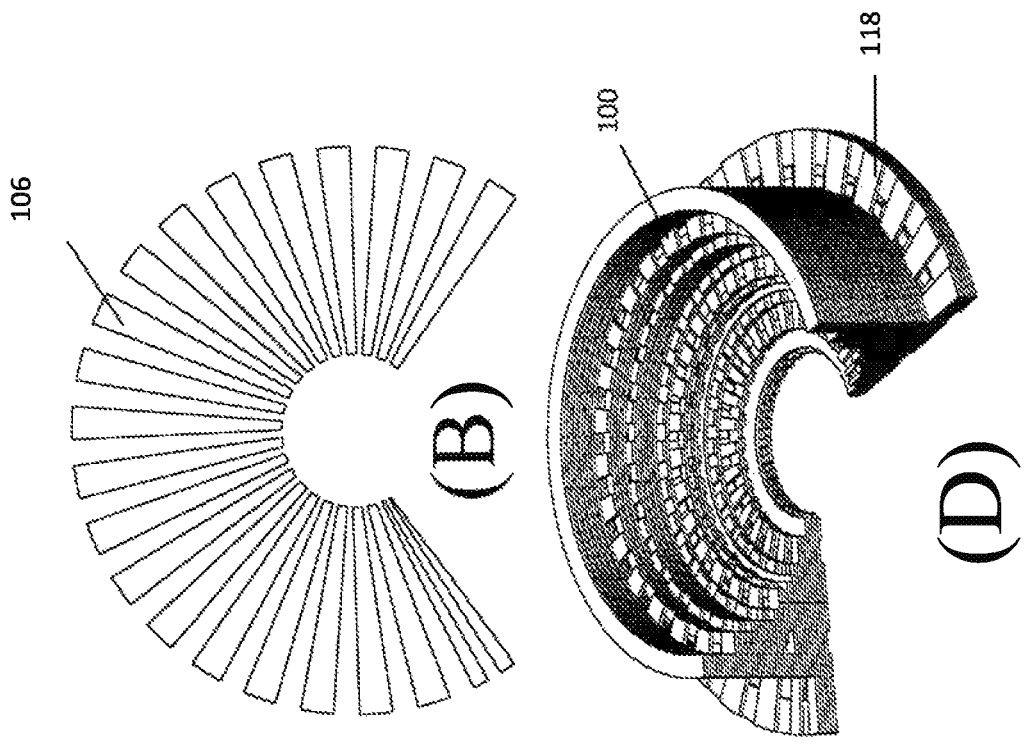
FIGS. 4A-4D (collectively referred to as "FIG. 4") provide illustrations that are useful for understanding an exemplary scaffold architecture.
Figure 4:
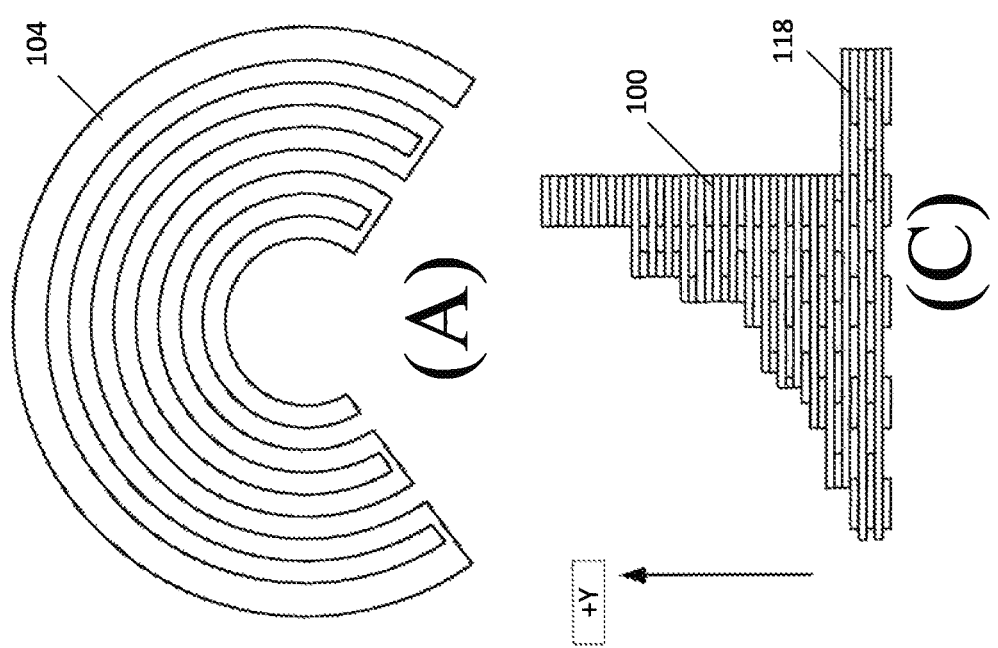

Referring now to FIG. 4, the scaffold 100 may, optionally, include one or more attachment segments or flaps 118 configured to flank or surround the meniscal rim of the remaining native tissue at the site of implant so as to provide fixation of the implant to tissue adjacent to the implantation site. For example, the flaps 118 may provide a mechanism to suture the partial meniscal scaffold 100 to the knee capsule or remaining native meniscus resulting in enhanced attachment of the scaffold and improved biomechanics of the knee joint following implantation. As a result, the flaps can help improve fixation of the scaffold to native tissue after implantation. The flaps also provide a substrate for cells to infiltrate from the synovium or the knee capsule. In an embodiment, a flap may be provided on the upper outer edge, the bottom outer edge, and/or both of the scaffold. Alternative locations are also possible.

FIGS. 4A-4D (collectively referred to as "FIG. 4") provide illustrations that are useful for understanding an exemplary scaffold architecture. FIG. 4A shows a single circumferential layer of filaments 104. FIG. 4B shows a single radial layer of filaments 106. FIG. 4C shows a cross-section of the scaffold 100 depicting the wedge shape characteristic of the scaffold and the optional flaps 118. FIG. 4D shows a 3D view of the complete scaffold 100 illustrating the polymer filament network 120 comprising the polymer filament network of alternating layers of circumferential fibers 104 and radial fibers 106, and the optional flaps.

As used herein, the term "synthetic polymer" refers to polymers that are not found in nature, even if the polymers are made from naturally occurring biomaterials. The term "natural polymer", as used herein, refers to polymers that are naturally occurring. The term "biocompatible", as used herein, refers to materials that, in the amounts employed, do not elicit a detrimental response in the host. The term "biocompatible", as used herein, is intended to include materials that may cause some inflammation, tissue necrosis or other immune responses when introduced into the host, provided that these effects do not rise to the level of pathogenesis. The term "bioresorbable", as used herein, refers to those materials that when placed in a living body at standard physiological conditions are degraded through either enzymatic, hydrolytic or other chemical reactions or cellular processes into by-products that are either integrated into or expelled from the body. It is recognized that in the literature, the terms "bioresorbable," "resorbable", "absorbable", "bioabsorbable" and "biodegradable" are frequently used interchangeably and such interchangeable meaning is intended for the present application.

Figure 5:
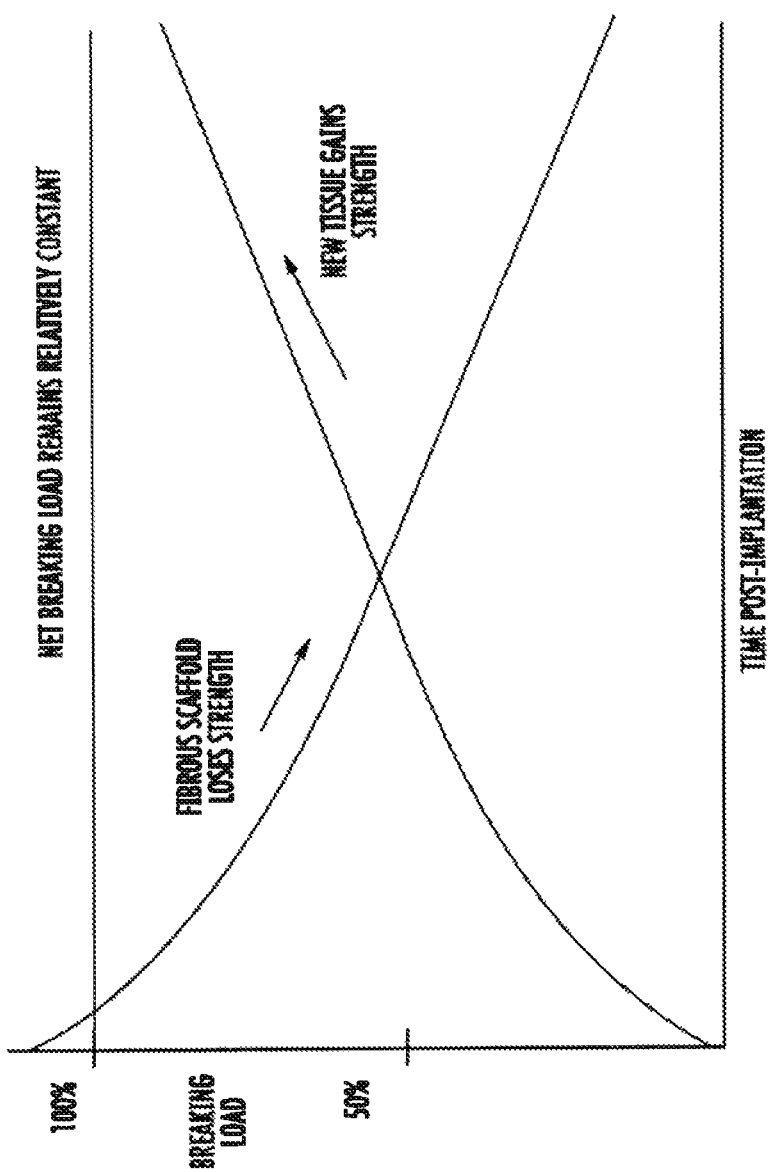
FIG. 5 presents a desirable degradation profiles for polymers suitable for use in instant devices.

In some scenarios, the scaffold 100 is formed from biodegradable material or materials. The polymers for the instant scaffold 100 are selected so the scaffold possesses mechanical properties which are the same or substantially similar to the mechanical properties of the native tissue being replaced. Moreover, as shown in FIG. 5, it is desirable for the mechanical properties of the scaffold to remain consistent as the scaffold is being remodeled. Accordingly, the polymers are selected so their degradation profile closely matches neo-tissue formation and remodeling, so the new tissue is afforded sufficient time to gain enough strength to compensate for the decrease in strength of the polymers. As shown in FIG. 5, this ensures that at all times the scaffold possesses mechanical properties resembling those of native tissue, which allows the scaffold to assume loads experienced in the joint at all times without failure.

Examples of suitable natural polymers include, but are not limited to, collagen, hyaluronic acid, fibrin glue, bone marrow, chitosan, alginates, celluloses, starches, silk, elastin, and other animal- or plant-derived proteins or polysaccharides. Suitable synthetic polymers include, but are not limited to, poly(alpha-hydroxy acids), poly(lactide-co-glycolide) (PLGA), poly(L-lactides) (PLLA), polylactides (PLA), polyglycolides (PGA); polyethylene, polypropylene, polyvinyl alcohol (PVA), polyethylene oxide (PEO); poly-p-dioxanone (PDO); polyarylates, polyacrylates, polycarbonates, polyesters, polycaprolactone (PCL), poly(desaminotyrosyl-tyrosine dodecyl ester dodecanoate) [p(DTD DD)], and combinations thereof. Suitable polyarylates and polycarbonates include, but are not limited to the tyrosine-derived polyarylates and polycarbonates disclosed by U.S. Pat. Nos. 5,099,060, 5,198,507, 5,216,115, 5,587,507, 5,658,995 and 6,048,521 (the disclosures of all of which are incorporated herein by reference).

In some scenarios, the matrix 102 is an amorphous structure composed primarily of Type I collagen. In addition to collagen, other types of materials may be added to alter the matrix properties as necessary or desired. For example, other proteins or proteoglycans may be used, including, but not limited to, glycosaminoglycans such as chondroitin sulfate, keratan sulfate, dermatan sulfate, heparin, heparin sulfate and hyaluronic acid. The percentage of these materials in the matrix may range between zero (0) and about twenty percent (20%) of the dry weight of the scaffold. The filaments for the polymer filament network 120 may preferably be made from a bioresorbable synthetic polymer (such as a [p(DTD DD)]) or a non-synthetic material (such as collagen).

The physical characteristics of the scaffold may be modified by using different materials for the matrix and/or 3D printing the filaments of the polymer filament network to have different diameters, mechanical strength, stiffness, or durability. Moreover, the physical characteristics of the scaffold may be modified by cross-linking the matrix, the polymer filament network or both. Cross-linking may be achieved by employing a variety of known methods including, but not limited to: chemical reaction with a carbodiimide, glutaraldehyde or formaldehyde among others; the application of energy such as gamma radiation, electron beam, UV light or microwave energy; dehydrothermal treatment in which water is slowly removed while the bone tissue is subjected to a vacuum; and enzymatic treatment.

A system and method for forming scaffold comprising a matrix and a polymer filament network will now be described with respect to FIGS. 6-9 and 11. Notably, the systems and methods are described herein in relation to the scaffold 100 of FIGS. 1-4. As discussed above, the scaffold comprises a matrix (e.g., matrix 102 of FIG. 1) designed to replace a biological soft tissue in a subject and a polymer filament network (e.g., polymer filament network 120 of FIG. 1) designed to provide structural support to the matrix. In an embodiment, the polymer filament network having a shape based on a shape of the target scaffold, is fabricated using a 3D printing system. The matrix material is then added to the printed polymer filament network, as discussed below.

Figure 6:
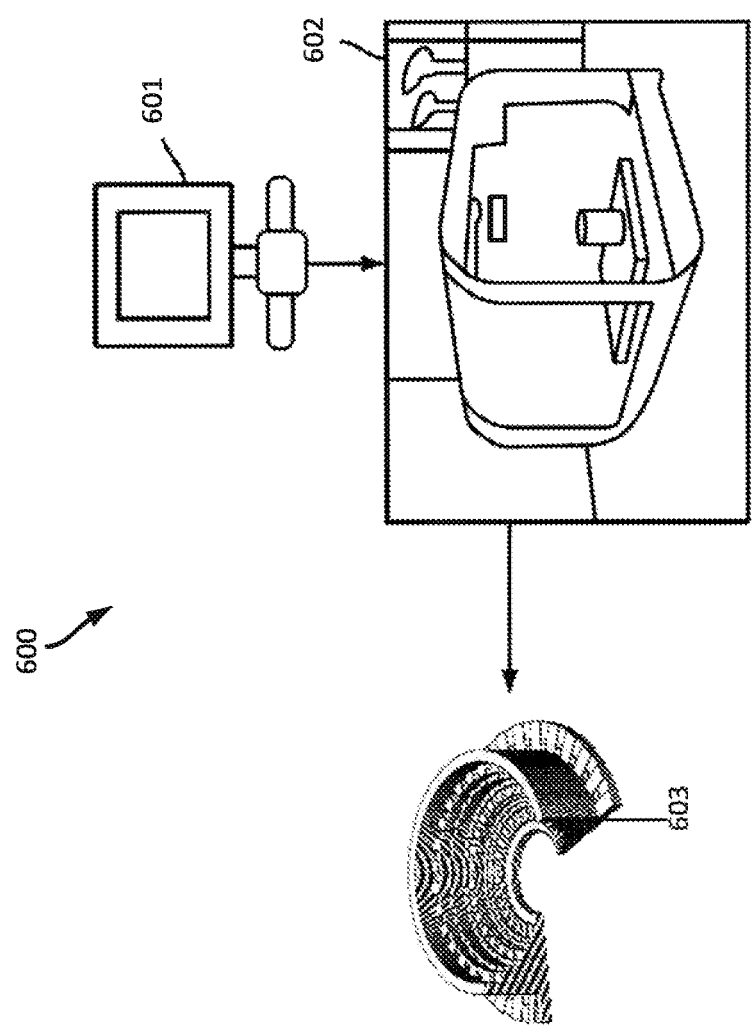
FIG. 6 illustrates a schematic representation of a system embodiment for fabricating a desired scaffold using a 3D printer.

FIG. 6 shows a schematic representation of a system 600 embodiment for fabricating the polymer filament network of a desired scaffold 603 using a 3D print device 602. The 3D print device 602 may be in communication with a computing device 601 having a memory device for storing programming instructions capable of designing and creating the polymer filament network via 3D printing. In some embodiments, the computing device 601 may be integral with the 3D print device 602.

Figure 7:
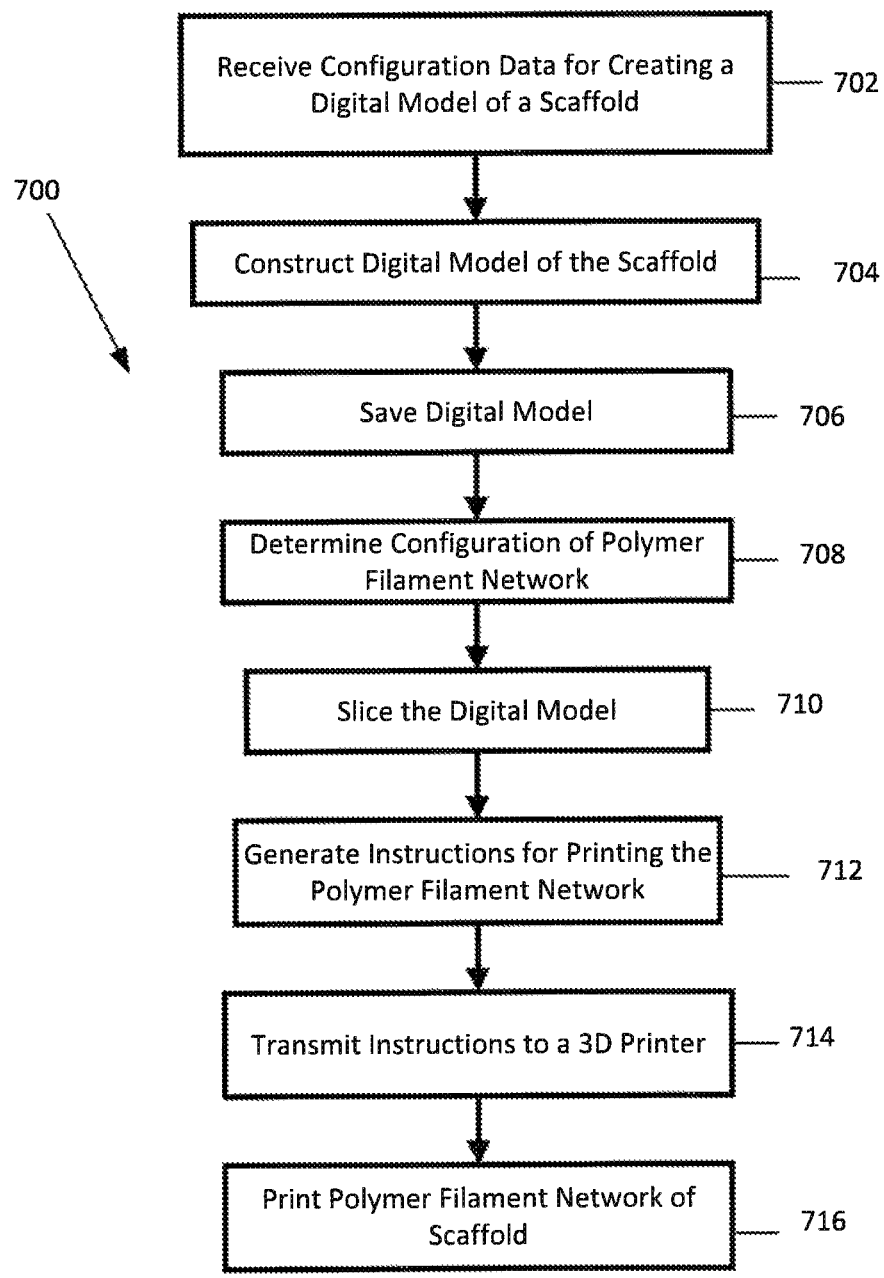
FIG. 7 illustrates a flowchart representation of an example method for fabricating the polymer filament network of a scaffold using a 3D printer.

Referring now to FIG. 7, an example method 700 for printing the polymer filament network of the scaffold of FIGS. 1-4 is illustrated. The process 700 illustrated in FIG. 7 and/or one or more steps thereof may be performed by a computing device (e.g., any device of FIG. 6). In other embodiments, the process illustrated in FIG. 7 and/or one or more steps thereof may be embodied in computer-executable instructions that are stored in a computer-readable medium, such as a non-transitory computer-readable memory. While the method 700 is described for the sake of convenience and not with an intent of limiting the disclosure as comprising a series and/or a number of steps, it is to be understood that the process does not need to be performed as a series of steps and/or the steps do not need to be performed in the order shown and described with respect to FIG. 7, but the process may be integrated and/or one or more steps may be performed together, or the steps may be performed in the order disclosed or in an alternate order.

The method 700 starts at 702 that includes receiving configuration data for creating a digital model of the desired scaffold. Examples of configuration data may include, without limitation, dimensions, shape, geometry, and build material of the scaffold and/or the polymer filament network. In an embodiment, the system may retrieve the configuration data from a database by querying a database for existing scaffolds. In another embodiment, the system may receive one or more parameters of the structural configuration from a user, via a user interface, and use the parameters to create the digital model. For example, a user may enter specific data associated with the target implant (e.g., left or right side of body, Medial-to-Lateral (ML) compartment width, Anterior-to-Posterior (AP) compartment length, and whether there is a shift in symmetry to one side or the other, size and/or shape of the partial scaffold). Additionally and/or alternatively, the system may receive configuration data from an image scanning device (e.g., a magnetic resonance imaging instrument (MRI), a nuclear imaging instrument, an ultrasound instrument or other imagining technology) configured to provide three-dimensional (3D) image data of the target tissue that will be replaced by the scaffold. The system may reconstruct a 3D model of the native tissue (i.e., the meniscus from the non-injured knee) from the image data received from the image scanning device and then extract the articulating surface geometry of the tissue from the 3D model. If two or more types of medical imaging devices are used, then the image data may be in a plurality of different data formats, and the system may transform the image data into a common data format.

The system may use the received configuration data to construct a digital model (704) of the scaffold, and save the digital model to a file format supported by a 3D printer or rapid prototyping machine (706). A digital model is a geometrical description and/or replica of the scaffold to be fabricated. A digital model may be a computer aided design ("CAD") model of the implant using, for example, a 3D CAD design software being executed by a computing device (e.g., a desktop computer). 3D CAD design software is well known in the art, and therefore will not be described herein in detail. Any known or to be known CAD design software can be used herein without limitation. For example, the present solution employs Solidworks 2014, AutoCAD, or 3D Studio Max. The present solution is not limited to particulars of this example. The system may save the digital model as, for example, an STL (stereolithography) file format, an AMF file format, or the like. For example, the CAD design software may include a virtual means (e.g., a widget) for enabling a user to export the CAD model to STL.

For example, the CAD design software may output a drop down menu item "Export To STL".

Once the digital model is created, the system may derive or determine (708) the configuration of the intended polymer filament network. The determination may be made by doing a geometrical analysis of the digital model relative to a large-scale knee MRI database. Alternative methods may also be utilized. The determined configuration preferably has the same shape as the soft tissue in need of replacement (e.g., the partial meniscus to be replaced).

At 710, the system may slice the saved digital model into slices and may generate (712) a machine code or instructions for printing the polymer filament network in the determined configuration. In an embodiment, the system may slice the saved digital model into two separate sets of slices—one for the radially-oriented filament layers of the polymer filament network, and one for the circumferentially-oriented filament layers of the polymer filament network. As such, each slice may correspond to either a circumferentially-oriented set of polymer filaments or a radially-oriented set of polymer filaments where that the circumferentially-oriented filaments and the radially-oriented filaments of the polymer filament network are printed in a repeating pattern of alternating layers. In such an embodiment, the slicing thickness used for slicing the digital model into layers corresponds to the thickness of the filaments of the intended polymer filament network. Alternatively and/or additionally, a plurality of slices may correspond to either a single layer of circumferential filaments or a single layer of radial polymer filaments. A user may then merge the two separate sets of slices to create the instructions for the 3D printer by adjusting parameters such as, without limitation, the thickness of each layer of filaments to be printed.

In an embodiment, the instructions for printing the horizontal layers may be formatted in accordance with any now or hereafter known programming language for computer-aided manufacturing to control automated machine tools such as a 3D printer (e.g., G-code). The machine code or instructions may include, without limitation, instructions for the operation of the 3D printer to print filaments of the polymer filament network in each of the individual layers of filaments based on desired height, width, and thickness parameters. For example, the G-code (or other code) may generate instruction data regarding movement of a nozzle of a 3D printer such as, without limitation, a printing direction and a printing area, data regarding printing property including material in accordance with respective layers. In an embodiment, the instructions also specify processing parameters such as, without limitation, melt temperature, extrusion pressure, printing head speed, and pre and post flow timing.

In an embodiment, the system may slice the saved digital model into layers using a set of parallel surfaces (planar or curved) sequentially to create layer data. The layer data may then be used to translate the STL file into instructions that are understood by the 3D printer. The layer data also includes paths definitions to fill the horizontal layers, and the instructions control 3D printer operations for printing the horizontal layers in accordance with the defined paths. Slicing method and software are also well known in the art, and therefore will not be described herein. The system may use any now or hereafter known slicing methods and slicing software without limitation. (for example, the present solution employs Slic3r or Bioplotter RP). For example, the digital model may be sliced to generate two-dimensional (2D) slices, and a Boolean operation can be performed slice-by-slice to generate combined 2D slices printable by a 3D printer. The 2D slices for example are parallel planes of the digital model. The combined 2D slices represent each layer of the polymer filament network and are printable by a 3D printer. Examples of the Boolean operation include AND, OR, XOR, etc. These operations may be used for joining, clipping, etc., of at least two objects to form a single object.

At 714, the system may transmit the instructions to a 3D printer, and the 3D printer may print 716 the polymer filament network of the scaffold in accordance with the instructions. In an embodiment, the 3D printer may print the polymer filament network such that the circumferentially-oriented filaments and the radially-oriented filaments are printed in alternate layers.

While the above disclosure describes a polymer filament network that includes 3D printed polymer filaments arranged in alternating layers of circumferential filaments and radial filaments, it will be understood to those skilled in the art, that the circumferential filament layers and the radial filament layers may not be alternating, without deviating from the principles of this disclosure. For example, the polymer filament network may be formed of a repeating pattern of two layers of circumferential filaments adjacent to each other and sandwiched between one or more radial layers of filaments.

Figure 8:
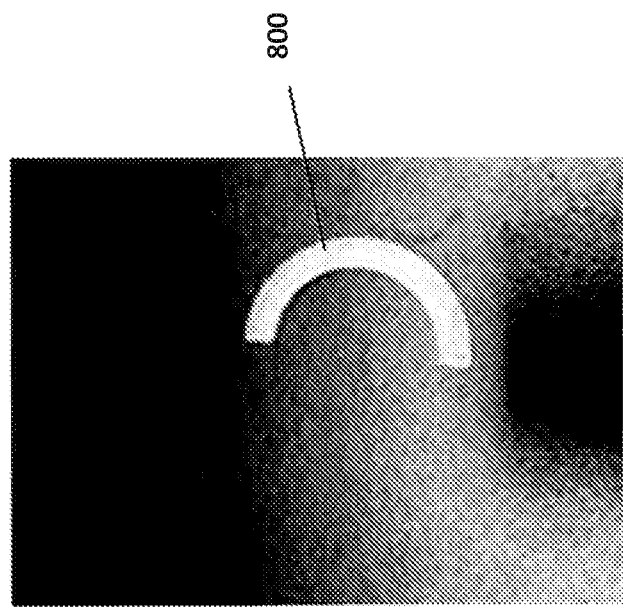
FIG. 8 is an image of an example support structure used for creating an optional flap in a scaffold.

In an optional embodiment, the system may create a flap in the scaffold by halting the printing of the polymer filament network before completion, prompting a user to place a support structure 800 (shown in FIG. 8) on the outer rim of partially printed network, and resuming printing of the polymer filament network thereafter. The print material is deposited over the support structure such that the support structure is removable after completion of the printing process. A flap is, therefore, created in the scaffold when the support structure is removed from the implant upon completion of the printing process. In an embodiment, the system may halt the printing of the implant before completion at a time that is calculated based on the position of the flap with respect to the top and/or bottom of the implant. For example, if a flap of height is to be created at top edge of the scaffold, the support structure may be placed by halting the printing process when the scaffold has been printed to a height of (H-h), where "H" is the thickness of the scaffold and "h" is the combined thickness of the support structure and the flap. As shown in FIG. 8, the support structure 800 preferably has a shape and a size that mimics the outer rim of the scaffold.

Upon completion of the printing process, polymer or other material (e.g., collagen) from which the matrix 102 is to be manufactured is added into the printed polymer filament network (i.e., the polymer filament network 120) to form the scaffold body, which is then solidified to form the scaffold 100.

For adding the matrix material to the mold assembly, the printed polymer filament network is placed upside down in a negative mold to form a mold assembly, and viscous matrix material such as collagen is placed on top of the mold assembly.

In an embodiment, the negative mold is a hollow structure configured to hold the printed polymer filament network that preferably has the same shape as the scaffold 100. In certain embodiments, the negative mold may be printed using the 3D printing process of FIG. 7 concurrently with the printing of the polymer filament network and/or separately. The mold assembly is then centrifuged until the collagen completely fills any void space within the filaments of the implant. For example, the mold assembly may be centrifuged at 650 g for thirty (30) minutes. Alternative methods may also be utilized. The polymer architecture of the scaffold is porous in order to allow for host cells to infiltrate the scaffold and remodel the native tissue (for example, the porous structure enhances absorption of blood during implantation and can increase the infiltration of inflammatory cells). The porous sponge configuration also increases the compressive properties of the scaffold closer to that of native tissue. The sponge also gives greater surface area for cells to infiltrate.

The process for solidifying the matrix 102 depends on the polymer used to form the matrix 102. For example, if collagen is used, the scaffold assembly may be lyophilized to remove water from the implant in order to create a porous sponge structure from the infused collagen. In some scenarios, the matrix may also be cross-linked to alter its physical characteristics. For example, the collagen may be cross-linked using a 1-ethyl-3-(3-dimethyl aminopropyl) carbodiimide (EDC)/N-hydroxysuccinimide (NHS) solution and lyophilized again. In an embodiment, the scaffold may be sterilized using gamma-irradiation.

As noted above, in some scenarios, both the polymer filament network 120 and the matrix 102 have same the shape and geometry as the soft tissue they are made to replace. For example, in implementations for the knee, the polymer filament network and the matrix may be constructed as a c-shaped disc with a wedge-like cross-section, similar to a knee meniscus. In an embodiment, the wedge shape may be created by shortening the radial filaments and reducing the number of circumferential filaments present in the +Y direction (See FIG. 4C). In addition, flaps that provide an extension to the knee capsule may optionally be created in the scaffold as shown in FIGS. 4C-4D.

Once fabricated, the unique arrangement of the polymer filament network in the scaffold allows for personalization of the scaffold size and geometry during partial meniscectomy based on the size and geometry of the tissue to be replaced by, for example, cutting or trimming of the c-shaped disc fabricated as described above. Upon cutting or trimming, the polymer filament network of the polymer filament network is not altered and fabricated scaffold does not lose its mechanical properties.

Figure 9:
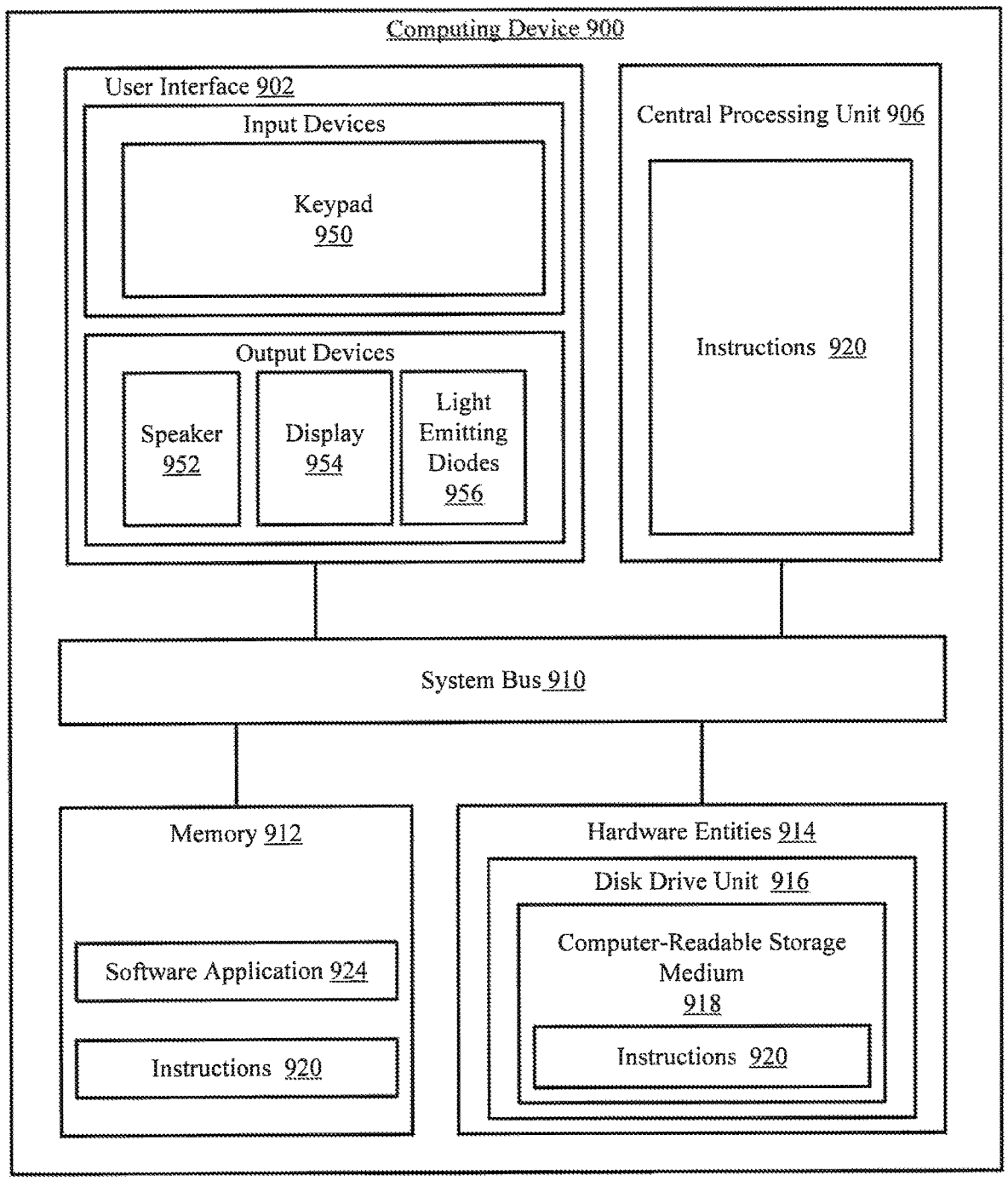
FIG. 9 is an illustration of an exemplary computing device that can be used to implement the present solution.

Referring now to FIG. 9, there is provided a detailed block diagram of an exemplary architecture for a computing device 900. The computing device can include, but is not limited to, a personal computer, a laptop computer, a desktop computer and/or a server. The CAD model and/or 3D printer instructions discussed above in relation to FIG. 7 is/are created using a computing device. This computing device is the same as or substantially similar to that shown in FIG. 9. As such, the following discussion of computing device 900 is sufficient for understanding certain computer processing operations performed herein to fabricate a scaffold.

Computing device 900 may include more or less components than those shown in FIG. 9. However, the components shown are sufficient to disclose an illustrative embodiment implementing the present solution. The hardware architecture of FIG. 9 represents one embodiment of a representative computing device configured to facilitate fabrication of an improved scaffold. As such, the computing device 900 of FIG. 9 implements at least a portion of a method for fabricating a 3D printed filament-reinforced scaffold in accordance with the present solution.

Some or all the components of the computing device 900 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 9, the computing device 900 comprises a user interface 902, a Central Processing Unit ("CPU") 906, a system bus 99, a memory 912 connected to and accessible by other portions of computing device 900 through system bus 99, and hardware entities 914 connected to system bus 99. The user interface can include input devices (e.g., a keypad 950) and output devices (e.g., speaker 952, a display 954, and/or light emitting diodes 956), which facilitate user-software interactions for controlling operations of the computing device 900.

At least some of the hardware entities 914 perform actions involving access to and use of memory 912, which can be a RAM, a disk driver and/or a Compact Disc Read Only Memory ("CD-ROM"). Hardware entities 914 can include a disk drive unit 916 comprising a computer-readable storage medium 918 on which is stored one or more sets of instructions 920 (e.g., software code) configured to implement one or more of the methodologies, procedures, or functions described herein. The instructions 920 can also reside, completely or at least partially, within the memory 912 and/or within the CPU 906 during execution thereof by the computing device 900. The memory 912 and the CPU 906 also can constitute machine-readable media. The term "machine-readable media", as used here, refers to a single medium or multiple media (e.g., a centralized or distributed database, and/or associated caches and servers) that store the one or more sets of instructions 920. The term "machine-readable media", as used here, also refers to any medium that is capable of storing, encoding or carrying a set of instructions 920 for execution by the computing device 900 and that cause the computing device 900 to perform any one or more of the methodologies of the present disclosure.

In some scenarios, the hardware entities 914 include an electronic circuit (e.g., a processor) programmed for facilitating the fabrication of a partial meniscus scaffold. In this regard, it should be understood that the electronic circuit can access and run a software application 924 installed on the computing device 900. The software application 924 is generally operative to: generating a digital model of partial meniscal scaffold having a reinforcing network of filaments; translate the digital model into a series of computer-readable instructions for a 3D printer; and communicate the computer-readable instructions to the 3D printer to print the reinforcing network of filaments. Other functions of the software application 1124 are apparent from the above discussion of the present solution.

In those or other scenarios, the medical-related data used to create the CAD model is encrypted so as to comply with HIPPA requirements. Any known or to be known encryption/decryption technique can be used herein without limitation. The translation involves selecting processing parameters. The processing parameters include, but are not limited to, selecting temperature, printing head speed, a pre-flow timing, and/or a post-flow timing.

Notably, the present solution can be implemented in a single computing device as shown in FIG. 9. The present solution is not limited in this regard. Alternatively, the present solution can be implemented in a distributed network system. For example, the present solution can take advantage of multiple CPU cores over a distributed network of computing devices in a cloud or cloud-like environment. The distributed network architecture ensures that the computing time of the statistics and enhanced functionality is reduced to a minimum, allowing end-users to perform more queries and to receive reports at a faster rate. The distributed network architecture also ensures that the implementing software is ready for being deployed on an organization's internal servers or on cloud services in order to take advantage of its scaling abilities (e.g., request more or less CPU cores dynamically as a function of the quantity of data to process or the number of parameters to evaluate).

3D printers are well known in the art, and therefore will not be described herein. Any known or to be known 3D printer can be used herein without limitation. The 3D printer uses the computer-readable instructions to print the partial meniscus implant.

Figure 10A:
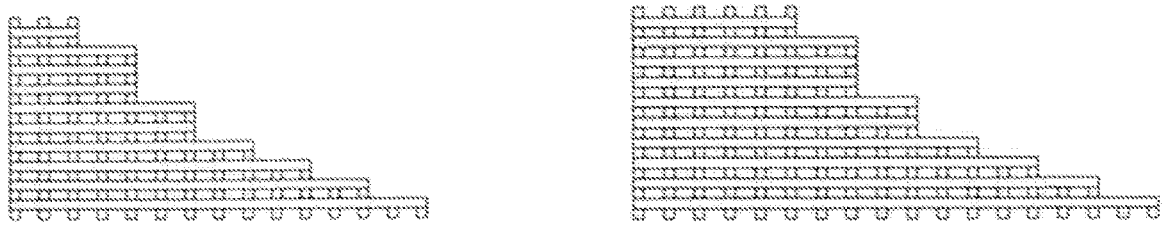
FIGS. 10A-10D (collectively referred to as "FIG. 10") provide illustrations that are useful for understanding different exemplar scaffold architectures.
Figure 10B:
Figure 10C:
Figure 10D:
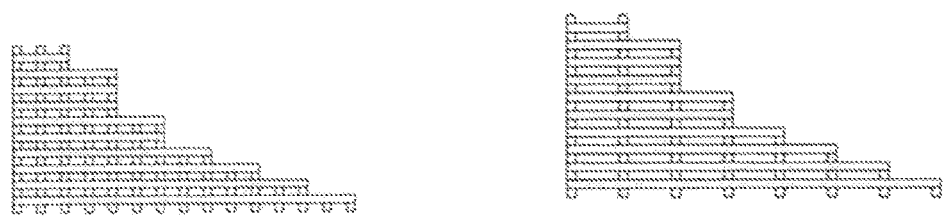

As discussed above, the scaffold is designed such that it has certain mechanical properties and geometric properties. For example, the scaffold is designed such that is has the same or substantially similar compressive properties as a native meniscus. The mechanical properties of the scaffold may be controlled by, for example, (a) filament diameter widths, (b) filament lengths, (c) number of circumferential filaments, (d) number of radial filaments, (e) filament spacing, and (e) polymer used to make the filaments. These parameters (a) and (b) also control cell growth on, around, and through the scaffold (which can be biodegradable). Values of these parameters (a) and (b) can be controlled by varying various printing parameters during the 3D printing process such that the scaffold has the desired compressive properties. The present solution is not limited to the particulars of this example. For example, in some scenarios, a scaffold is created with varying widths by increasing the total number of circumferential filaments and increasing the length of the radial filaments. FIG. 10A illustrates this scaffold architecture. In other scenarios, the scaffold is created with a varying proximal surface contour by varying the number of circumferential filaments in each layer and the length of the radial layers. FIG. 10B illustrates this scaffold architecture. In yet other scenarios, the scaffold is created with varying density by varying the spacing between each filament. FIG. 10C illustrates this scaffold architecture. In other scenarios, the scaffold is created with varying compressive properties and tensile properties by varying the spacing between each filament. FIG. 10D illustrates this scaffold architecture. In other scenarios, the scaffold is created from various imaging modalities to manufacture a personalized scaffold.

In some scenarios, scaffolds of various sizes can be fabricated in accordance with the present solution. For example, scaffolds can be made in standard small, medium and large sizes. At the time of surgery, a medical practitioner may trim or cut a standard size scaffold to an appropriate size for the given patient based on the size of the tissue to be replaced (as shown in FIGS. 2A and 2B). The present is not limited to the particulars of this example.

In other scenarios, the scaffolds are fabricated or 3D printed so as to be personalized to any given patient. For example, one or more imaging devices (e.g., an MRI device and/or X-ray device) is(are) used to acquire images of a portion of a patient's body. The image data is then provided to equipment for purposes of fabricating a personalized scaffold for the patient. The personalized scaffold can be fabricated at the medical practitioner's facility or another remote facility. The present is not limited to the particulars of this example.

The following EXAMPLES are provided in order to further illustrate the present solution. The scope of the present solution, however, is not to be considered limited in any way thereby.

Example 1: Mechanical Evaluation of Tensile and Compressive Properties

Figure 11:
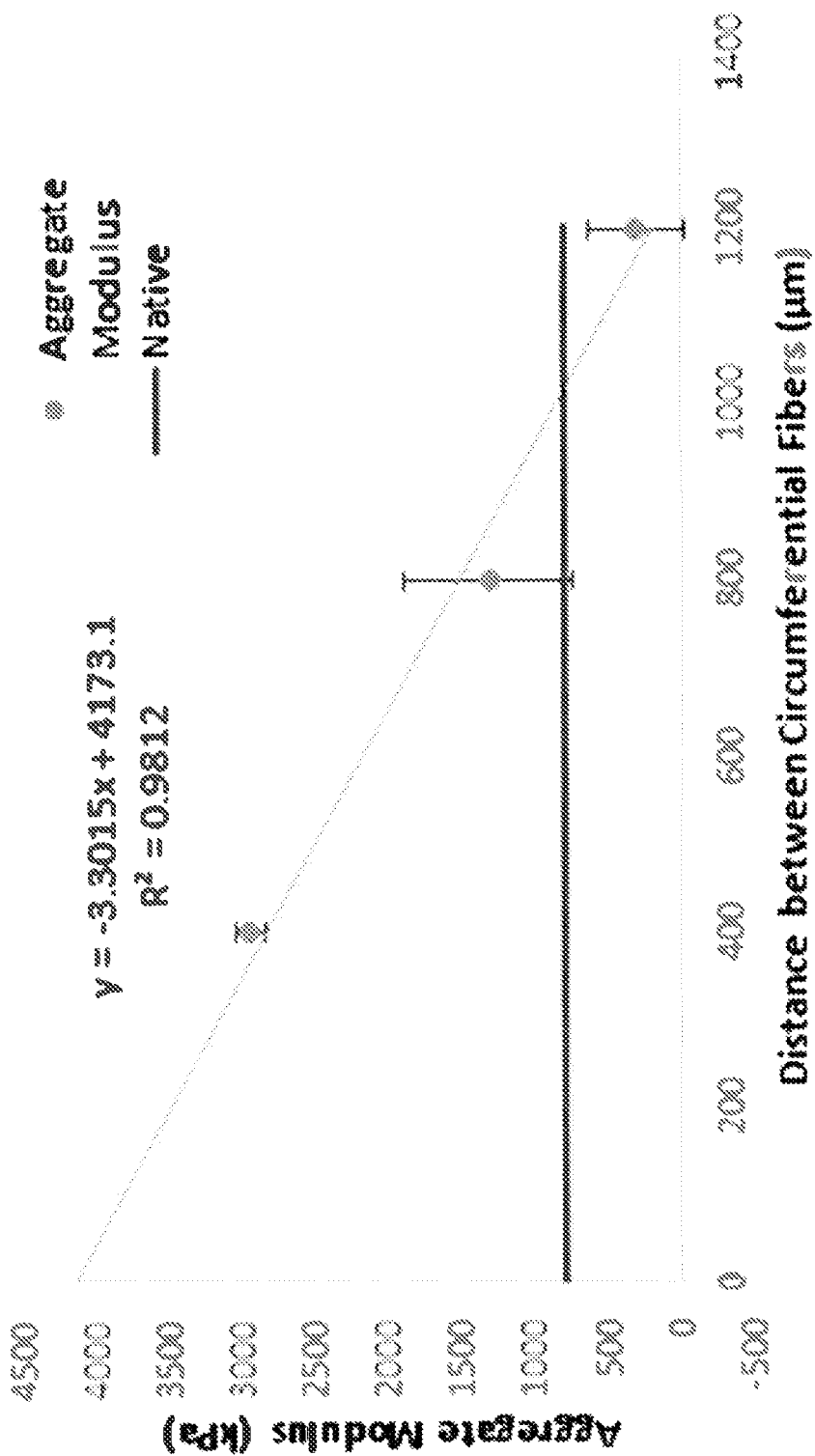
FIG. 11 illustrates a graphical representation of preliminary data generated from polycaprolactone (PCL) for analyzing the aggregate compressive modulus of the scaffold when tested in confined compression creep and analyzed using Mow's biphasic theory.

A preliminary mechanical evaluation was carried out using Mow's Biphasic Theory described in MOW, V. C., et al., Biphasic Creep And Stress Relaxation Of Articular Cartilage In Compression? Theory And Experiments. Journal of Biomedical Engineering. 1980, Vol. 102, No. 1, pages 73-84. Three polymer filament network assemblies were printed by depositing polycaprolactone (PCL) according to a digital model of the scaffold, with varying spacing between the circumferential filaments. The 3D printing was performed at a speed of 2 mm/s using a 400 micron inner diameter needle at 6.4 bar pressure and 145° C. temperature on a 3D Bioplotter (EnvisionTEC, Dearborn, Mich.) at the New Jersey Center for Biomaterials (Department of Chemistry, Rutgers University, Piscataway, N.J.). The spacing between the circumferential filaments was varied from 400 microns, 800 microns, and 1200 microns. This resulted in a linear decrease in the aggregate compressive modulus of the scaffold when tested in confined compression creep and analyzed using Mow's Biphasic Theory (FIG. 11). This is novel and important considering the current commercial partial meniscus scaffolds have considerably weaker compressive properties than the native meniscus.

Example 2: The Scaffolds were Fabricated Using the Methods Described Herein, and Evaluated by Characterizing the Mechanical Properties and Comparing to Those of Ovine Native Meniscus (i) Fabrication of Meniscus Scaffolds.

Polymer filament network filament assemblies were printed by depositing poly(desamino-tyrosyl-tyrosine dodecyl ester dodecanoate) [p(DTD DD)] at a speed of 1.2 mm/s using a 400 micron inner diameter needle at 9 bar pressure and 160° C. temperature on a 3D Bioplotter (EnvisionTEC, Dearborn, Mich.) at the New Jersey Center for Biomaterials (Department of Chemistry, Rutgers University, Piscataway, N.J.). The average print time was 142±3 min.

The reinforcing filament assemblies were infused with collagen and hyaluronic acid. Sodium hyaluronate (0.25 g/L; molecular weight 1.5-2.2 MDa, Acros Organic, Bridgewater, N.J.) was dissolved in dilute hydrochloric acid (pH 2.35). A collagen dispersion was made by swelling lyophilized type I bovine collagen in the acid solution. The appropriate amount of collagen was added to a volume of acid (e.g. for 1% dispersion, 1.0 g collagen added to 100 ml acid). As noted above, in different embodiments, other materials may be added to alter the properties of the matrix portion and dispersion concentrations may be modified. The collagen/acid mixture was then homogenized using a high speed blender (pulse blending to reduce possible heat denaturation effects on collagen). After about five minutes of pulse blending (mix ~5 seconds, wait for ~1 minute), the mixture was de-aerated under vacuum for about five minutes. The 3D printed reinforcing filament assemblies were infused with the collagen/acid mixture, frozen, and lyophilized to form the scaffolds. The scaffolds were cross-linked with 10 mM, 1-ethyl-3-(3-dimethaylaminopropyl)carbodiimide hydrochloride and 5 mM N-hydroxysuccinimide for 6 hours. The resulting scaffolds were rinsed three times for 10 minutes in DI water, one time for 3 hours in 100 mM sodium phosphate, and rinsed for 24 hours in DI water. Scaffolds were then frozen, lyophilized, and sterilized with 25 kGy of gamma irradiation (Sterigenics, Rockaway, N.J.).

(ii) Mechanical Evaluation.

A Student's t-test was performed in Microsoft Excel 2016 to compare the confined compressive creep, circumferential tensile, and pull-out testing between native ovine meniscus and the scaffold (discussed below). A repeated-measures analysis of variance (ANOVA) with a post-hoc Sidak's test was performed for the contact stress analysis using Minitab Version 17. For all tests, statistical significance was defined as $p<0.05$.

(a) Scaffold Properties:

The 3D printed polymer network of each scaffold was weighed after printing (polymer weight). The scaffold was weighed after completion of all fabrication steps (scaffold weight). The percent polymer and percent collagen were calculated from these values. The dry scaffolds were weighed, hydrated in phosphate buffered saline (PBS) for at least one hour, and weighed again. Swelling ratio was calculated as the ratio of the hydrated mass to the dry mass (n=6).

Scaffold porosity was determined through an ethanol infiltration assay. A 4 mm diameter biopsy punch was removed from dry scaffolds (n=6) and trimmed to obtain a cylindrical sample. The height was measured using Vernier calipers and the dry mass was measured ($m_{dry}$). The samples were soaked in 100% ethanol for one hour, superficially dried, and the mass was immediately measured (me).

The porosity was found by dividing the pore volume by the total volume, as demonstrated by the following equation:

$$\% \text{ porosity} = \frac{m_e - m_{dry}}{\rho V} \times 100\%$$

where, $\rho$ represents the density of ethanol (0.789 mg/ml) and V represents the volume of the sample.

The total scaffold mass was 549±72 mg with a polymer mass of 504±60 mg and a collagen mass of 41±21 mg. This corresponds to an average of 92% polymer and 8% collagen. The scaffold swelling ratio was 364±58%, and the scaffold porosity was 69.9±8.0%.

(b) Confined Compressive Creep

Four mm diameter×3 mm height cylindrical plugs were taken from the anterior, body, and posterior regions of scaffolds and native menisci (n=12, 4×3 regions). The hydrated plugs were placed in a 4 mm diameter cylindrical chamber with a unidirectional fluid flow filter. A 1 N load was applied for 3600 seconds (model 5542; Instron, Canton, Mass.). The instantaneous compressive modulus was calculated from the initial loading phase from 0.5 N to 1 N. The aggregate moduli and permeability of the samples were calculated according to Mow's Biphasic Theory.

Figures 12A, 12B:
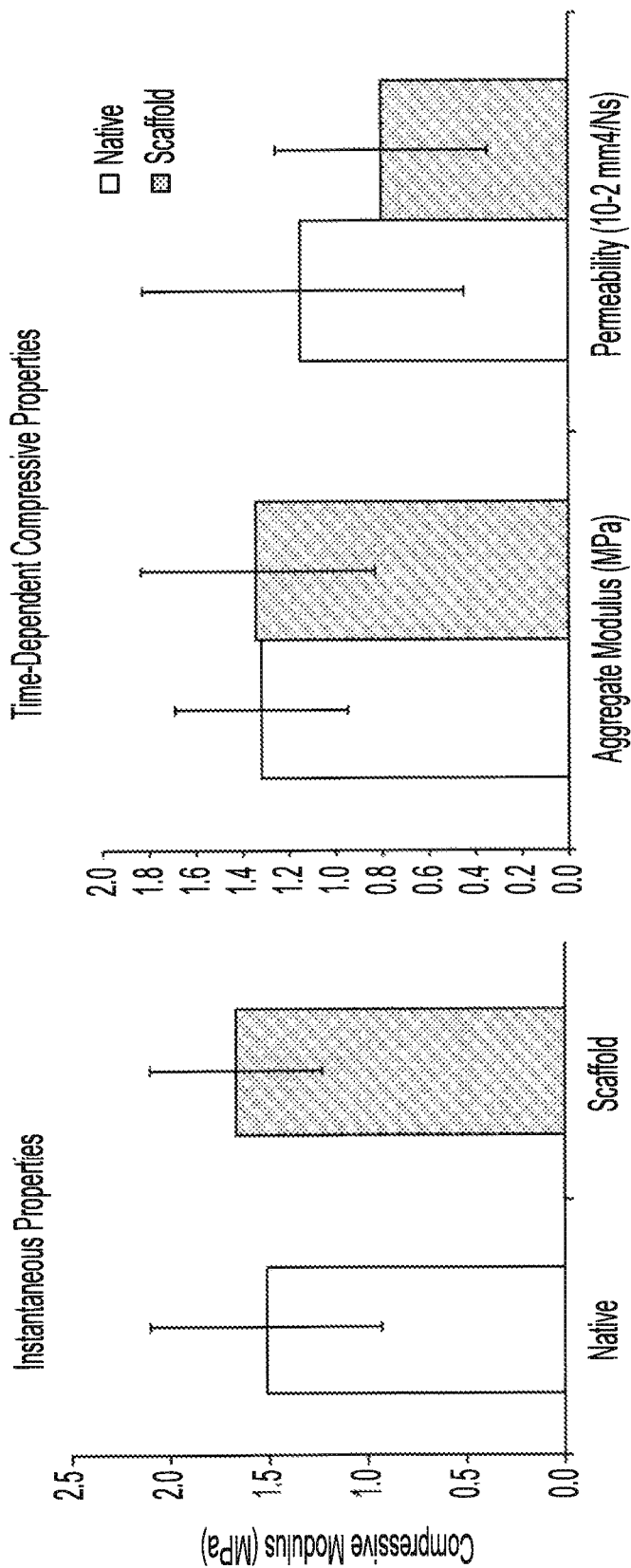
FIG. 12A illustrates the instantaneous compressive modulus.
FIG. 12B illustrates the aggregate modulus and permeability of native ovine meniscus and scaffold (n=4 from the anterior, body, and posterior regions). The values indicated represent mean±SD.

The scaffold matched both the instantaneous and time-dependent compressive properties of the native meniscus (FIGS. 12A and 12B). The instantaneous compressive modulus of the scaffold (1.66±0.44 MPa) and native meniscus (1.52±0.59 MPa) were comparable (p=0.26). The aggregate modulus was nearly identical (p=0.93) between the scaffold (1.33±0.51 MPa) and the native meniscus (1.31±0.36 MPa). The permeability was not significantly different (p=0.075).

(c) Circumferential Tensile Testing

Figure 13:
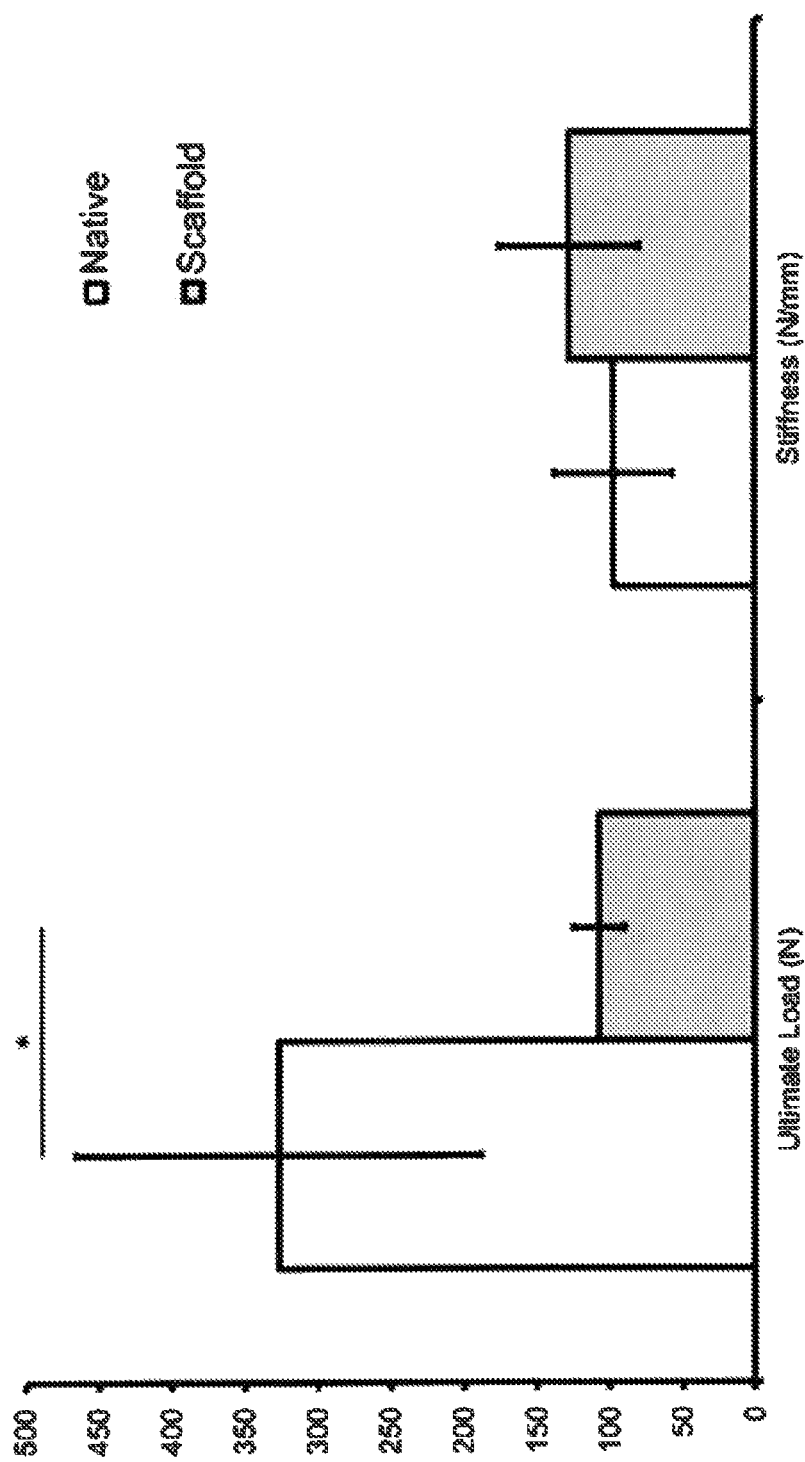
FIG. 13 illustrates the ultimate tensile load and tensile stiffness of scaffold compared with native ovine menisci (n=6/group). The values indicated represent mean±SD. (*Denotes statistically significant difference ($p<0.05$)).

Scaffolds and native menisci (n=6/group) were hydrated in PBS at room temperature for at least one hour. Each scaffold or meniscus was loaded into cryogenic freeze clamps (TA Instruments New Castle, Del.) with an 8 mm gage length encompassing the central region. The samples were loaded in tension at a rate of 10 min/min to failure (model 5592; Instron, Canton, Mass.). Circumferential tensile stiffness and ultimate tensile load were calculated for each sample. FIG. 13 illustrates the ultimate tensile load and tensile stiffness of the scaffold compared with native ovine meniscus.

The tensile stiffness of the scaffold (127.6±47.6 N/mm) was 31.4% greater (p=0.953) than the native ovine meniscus (97.1±40.3 N/mm). The ultimate tensile load of the scaffold was 33% of that of the native ovine meniscus (p<0.01).

(d) Suture Retention Testing

Suture retention testing was performed on scaffolds and native menisci (n=6 each). A 2-0 Ethibond suture was placed radially in a vertical mattress fashion, 2 mm from the outer margin of samples. Two gripping sutures were placed through the sample on either side of the Ethibond suture, reinforced with cardiovascular pledgets, and looped around the outer margin. The Ethibond suture was loaded in tension at 50 mm/min until failure using known methods. Mode of failure was recorded, and the pull-out load and stiffness were calculated.

Figures 14A, 14B:
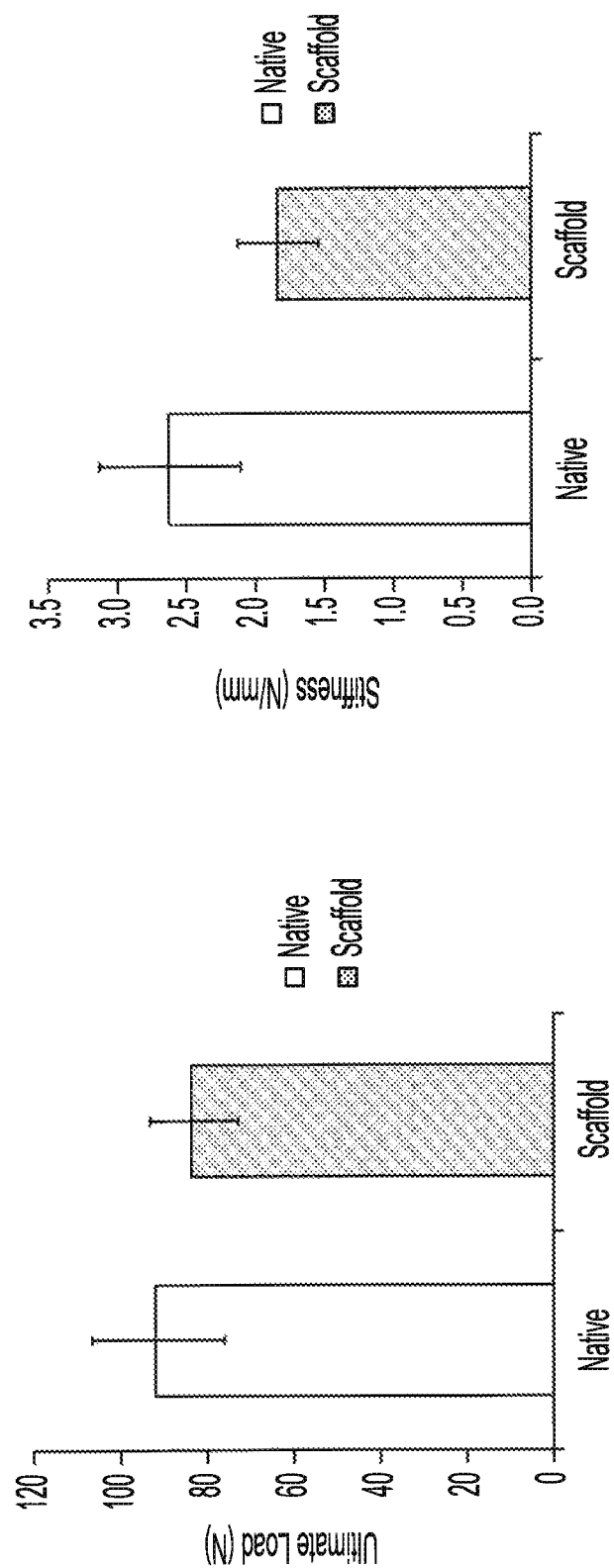
FIG. 14A illustrates the pull-out ultimate load of native ovine meniscus and the scaffold.
FIG. 14B illustrates the stiffness of native ovine meniscus and the scaffold. The values indicated represent mean±SD.

The suture pulled out of the scaffold 6 out of 6 samples, whereas for the native condition, the suture failed in 4 samples and the suture pulled out of 2. The scaffold (83.1±10.0 N) possessed a similar ultimate pull-out load (p=0.25) to the native meniscus (91.5±15.4 N). The stiffness of the scaffold fixation was 30% less than that of the native meniscus (FIGS. 14A and 14B).

(e) Contact Stress Testing

Fresh frozen ovine hind limbs with varying sized menisci (skeletally mature, 4-8 years old) were obtained from Colorado State University (n=6). The skin, subcutaneous fat, muscle, and patella were removed, taking care to preserve the cruciate ligaments, collateral ligaments, and capsule. The tibia and femur were transected about 3 cm below and 10 cm above the joint line, respectively. The tibia was potted in polymethylmethacrylate and allowed to cure for 30 minutes. Bone tunnels were drilled in the femur at 30° and 60°, allowing for natural rotation and varus-valgus alignment of the femoral condyles at each angle.

All joints were inspected prior to testing for signs of meniscal or cartilage damage. For testing, the anterior and posterior capsule were transected just under the medial meniscus to allow for insertion of a pressure-sensitive sensor (K-Scan #4000, Tekscan Inc.). The Tekscan strip was trimmed to the width of the medial compartment and covered in Tegaderm Transparent Film (3M, St. Paul, Minn.). Prior to testing, the Tekscan strip was preconditioned five times at 1500N, and calibrated at 250 N and 1000 N. The strip was covered in petroleum jelly, a suture was placed through the leading edge of the strip, and the suture was pulled to place the strip under the medial meniscus. The MCL was released at the femoral attachment and reattached with suture endobutton technique (Smith and Nephew, Andover, Mass.).

The knee was loaded into a custom jig in an Instron (model 5592; Instron, Canton, Mass.), maintaining natural alignment of the joint. Following hydration, a 200 N load was applied at 30 mm/min on the medial compartment for 5 cycles of preconditioning followed by 15 cycles of testing. The peak contact pressure, mean contact pressure, and contact area were calculated for each cycle and averaged for each knee in MATLAB (R2015b, Mathworks, Natick, Mass.). The knee was tested with the intact meniscus, autograft, scaffold, and 80% (measured in relation to the meniscal radial width) partial meniscectomy. The autograft, scaffold, and partial meniscectomy were placed on the posterior region on the meniscus. Although autograft does not represent a realistic clinical option, it did provide a positive control as it possessed the ideal material properties of the native meniscus. The autograft and scaffold were sutured with 2-0 Ethibond sutures (Ethicon, Somerville, N.J.) with 2 sutures running radially and 2 sutures circumferentially.

Figure 15A:
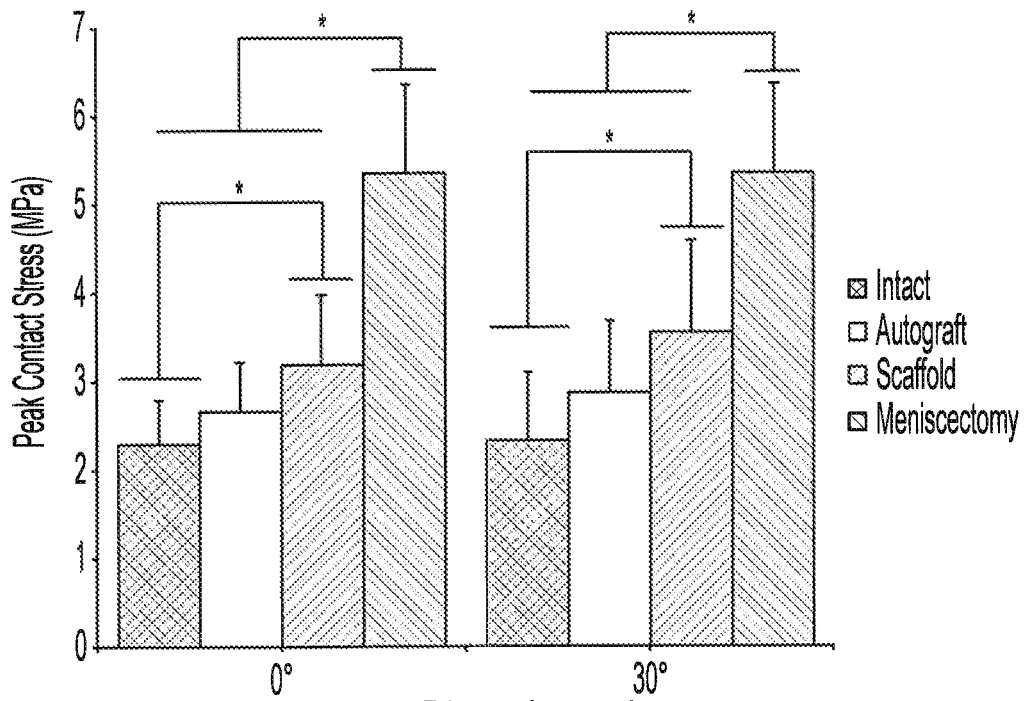
FIG. 15A depicts peak contact stress.
Figure 15B:
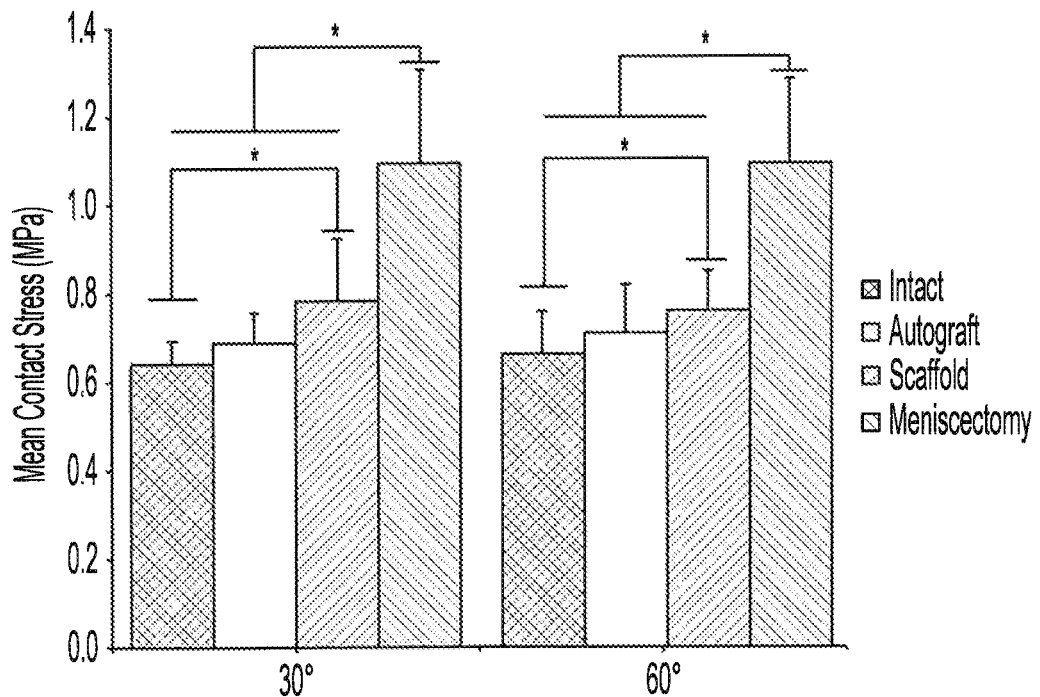
FIG. 15B depicts mean contact stress.
Figure 15C:
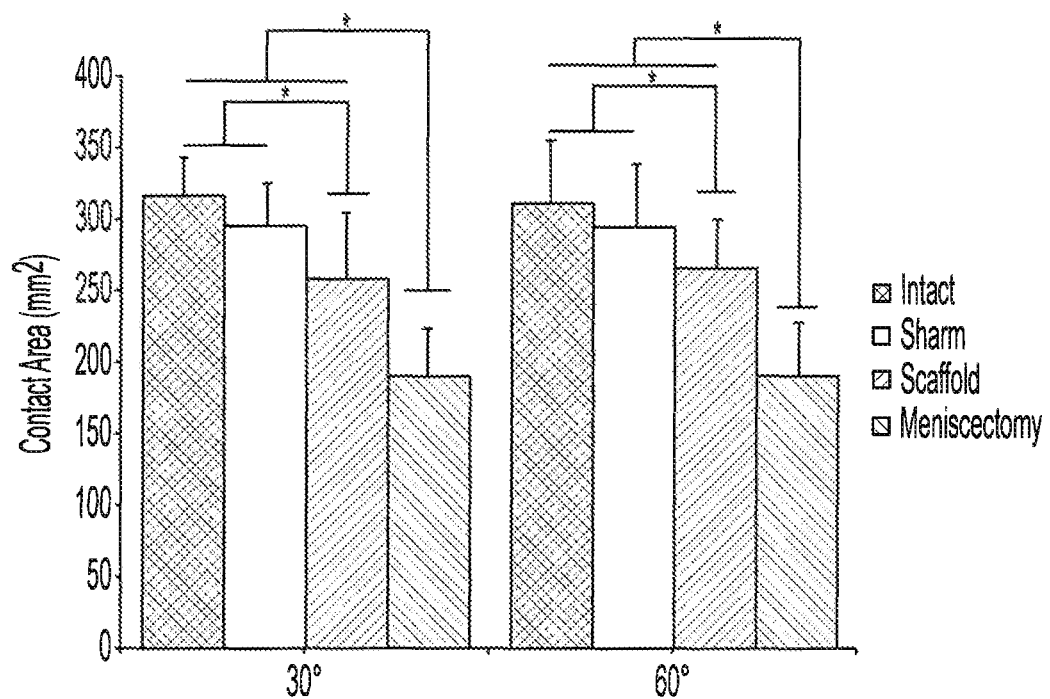
FIG. 15C depicts contact area for intact, autograft, scaffold, and partial meniscectomy conditions. The values indicated represent mean±SD. (*Denotes statistically significant difference ($p<0.05$)).

Angle of flexion did not affect the contact mechanics of the ovine stifle joint for any condition (p=0.988). The scaffold performed equivalently to autograft for mean contact stress (p=0.079), peak contact stress (p=0.103), but differed in contact area (p=0.001). Relative to meniscectomy, the scaffold reduced peak contact stress by 60-67% and increased contact area by 138% (FIG. 15). Partial meniscectomy demonstrated significantly greater peak and mean contact stress and significantly less contact area than all other conditions. Compared to the intact condition, the joint experienced progressive increases in peak contact stresses of 20%, 45%, and 130% and mean contact stress of 7%, 18%, and 167%, for autograft, scaffold, and meniscectomy, respectively. Likewise, the contact area successively decreased by 6%, 16%, and 40%, respectively.

As is apparent from the mechanical testing of the scaffolds fabricated using the methods described herein, the fabricated scaffolds closely mimic the structural properties of native ovine meniscus and restore the load-distributing properties following partial meniscectomy of the ovine knee joint. As such, the scaffold of the present disclosure has the potential to delay, or possibly prevent, the onset of osteoarthritis caused by partial meniscectomy. The aforementioned mechanical parameters all contribute to the device's ability to distribute loads in the joint. In addition, scaffolds with compressive moduli that closely match those of the native meniscus induce greater fibrocartilage formation. With compressive properties and tensile stiffness similar to that of native tissue, the suture retention properties of the fabricated scaffold also validated implantation of the device.

In an embodiment, the scaffold may be configured to have an instantaneous compressive modulus that is about 80% to about 140%, about 90% to about 130%, and about 100% to about 120% of the instantaneous compressive modulus of native meniscus. Preferably, the scaffold may be configured to have an instantaneous compressive modulus that is about 80% to about 138% of the instantaneous compressive modulus of native human meniscus.

In an embodiment, the scaffold may be configured to have an aggregate compressive modulus of about 65% to about 140%, about 70% to about 130%, about 80% to about 120%, and about 90% to about 110% aggregate compressive modulus of native human meniscus. Preferably, the scaffold may be configured to have an aggregate compressive modulus that is about 68.6% to about 140% of the aggregate compressive modulus of native meniscus.

In an embodiment, the scaffold may be configured to have a permeability of about 55% to about 230%, about 65% to about 220%, about 75% to about 210%, about 85% to about 200%, about 95% to about 190%, about 110% to about 180%, about 120% to about 170%, about 130% to about 160% of the permeability of native human meniscus. Preferably, the scaffold may be configured to have a permeability that is about 57.5% to about 227.5% of the permeability of native human meniscus.

In an embodiment, the scaffold may be configured to have a tensile stiffness of about 80% to about 180%, about 90% to about 170%, about 100% to about 160%, about 110% to about 150%, about 120% to about 140% of the tensile stiffness of native meniscus. Preferably, the scaffold may be configured to have a tensile stiffness that is about 82.4% to about 180.4% of the permeability of native human meniscus.

As noted above, intervertebral discs or temporomandibular joint discs function as load transmitters and distributors to prevent high-stress bone-on-bone contact. For example, an intervertebral disc comprises the annulus fibrosus and the nucleus pulposus. The nucleus pulposus is the inner gelatinous material surrounded by the annulus fibrosus. The nucleus pulposus distributes mechanical loads placed upon the disc, while the annulus fibrosus provides structural integrity and constrains the nucleus pulposus to a specific spinal region. The annulus fibrosus has an internal structure which is very similar to the internal structure of meniscal tissue. Accordingly, concepts herein described may be utilized to construct scaffolds for full or partial replacement of annulus fibrosus by, for example, constructing toroidal scaffolds.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods and sequence of steps of the method without departing from the concept, spirit and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

We claim:

1. A resorbable scaffold for partial meniscus regeneration comprising:
   a polymer filament network comprising a first plurality of layers comprising circumferentially-oriented filaments alternating with a second plurality of layers comprising radially-oriented filaments, the polymer filament network having a wedge-shaped cross-section between a first layer and a second layer, wherein:
   a number of the circumferentially-oriented filaments sequentially decreases in at least some of the first plurality of layers from the first layer to the second layer, and
   a length of the radially-oriented filaments sequentially decreases in at least some of the second plurality of layers from the first layer to the second layer; and
   a matrix embedded in the polymer filament network.

2. The resorbable scaffold of claim 1, wherein the first plurality of layers comprising the circumferentially-oriented filaments alternating with the second plurality of layers comprising the radially-oriented filaments form a repeating pattern such that cutting of the resorbable scaffold into a desired geometrical shape or size does not alter one or more mechanical properties of the resorbable scaffold.

3. The resorbable scaffold of claim 1, further comprising an attachment flap extending from an outer edge of the resorbable scaffold and configured to provide a substrate for cells to infiltrate after implantation of the resorbable scaffold from a host environment.

4. The resorbable scaffold of claim 3, wherein the attachment flap is configured to extend outwardly from an upper outer edge or a lower outer edge of the resorbable scaffold.

5. The resorbable scaffold of claim 1, wherein a number of the circumferentially-oriented filaments is more than a number of the radially-oriented filaments in the polymer filament network to provide a higher tensile strength in a circumferential direction compared to a radial direction of the resorbable scaffold.

6. The resorbable scaffold of claim 1, wherein the resorbable scaffold is fabricated in the shape of a knee meniscus.

7. The resorbable scaffold of claim 1, wherein the circumferentially-oriented and the radially-oriented filaments of the polymer filament network are fabricated from a bioresorbable material selected such that a rate of degradation of the bioresorbable material is sufficiently long so as to allow for tissue ingrowth to occur within the bioresorbable material.

8. The resorbable scaffold of claim 1, wherein the matrix is fabricated from a bioresorbable material selected from the group consisting of proteins, proteoglycans, biocompatible natural polymers, biocompatible synthetic polymers, and combinations thereof.

9. The resorbable scaffold of claim 1, wherein the matrix is fabricated from proteins comprising collagen.

10. The resorbable scaffold of claim 9, wherein the collagen is lyophilized and cross-linked.

11. The resorbable scaffold of claim 1, wherein the polymer filament network is fabricated by three-dimensional (3D) printing.

12. The resorbable scaffold of claim 1, wherein filaments of the polymer filament network are formed from poly (desamino tyrosyl-tyrosine dodecyl ester dodecanoate).

13. The resorbable scaffold of claim 1, wherein a distance between each of the circumferentially-oriented filaments of the polymer filament network is inversely proportional to an aggregate compressive modulus of the resorbable scaffold.

14. The resorbable scaffold of claim 1, wherein one or more mechanical properties of the resorbable scaffold depend upon one or more of the following: diameter of the circumferentially-oriented filaments, length of the circumferentially-oriented fibers, a number of the circumferentially-oriented filaments, distance between each of the circumferentially-oriented filaments, diameter of the radially-oriented fibers, length of the radially-oriented fibers, a number of the radially-oriented filaments, distance between each of the radially-oriented filaments, or material of filaments of the polymer filament network.

15. The resorbable scaffold of claim 1, wherein the resorbable scaffold is a knee meniscus implant configured to have at least one mechanical property that is substantially similar to that of a native meniscus.

16. The resorbable scaffold of claim 15, wherein an instantaneous compressive modulus of the resorbable scaffold is about 80% to about 140% of an instantaneous compressive modulus of the native meniscus.

17. The resorbable scaffold of claim 15, wherein an aggregate compressive modulus of the resorbable scaffold is about 65% to about 140% of an aggregate compressive modulus of the native meniscus.

18. The resorbable scaffold of claim 15, wherein a tensile stiffness of the resorbable scaffold is about 80% to about 180% of a tensile stiffness of the native meniscus.

\* \* \* \* \*

UNITED STATES PATENT AND TRADEMARK OFFICE
CERTIFICATE OF CORRECTION

| | | |
|---|---|---|
| PATENT NO. | : 11,116,640 B2 | Page 1 of 1 |
| APPLICATION NO. | : 16/484901 | |
| DATED | : September 14, 2021 | |
| INVENTOR(S) | : Salim A. Ghodbane et al. | |

It is certified that error appears in the above-identified patent and that said Letters Patent is hereby corrected as shown below:

In the Specification

At Column 1, Line number 16, enter the following:
STATEMENT REGARDING FEDERALLY SPONSORED RESEARCH
This invention was made with government support under grant number W81XWH-14-2-0003 awarded by the Defense Health Agency, Medical Research and Development Branch. The government has certain rights in the invention.

Signed and Sealed this
Twenty-second Day of April, 2025

Coke Morgan Stewart
*Acting Director of the United States Patent and Trademark Office*